(12) United States Patent
Seul et al.

(10) Patent No.: US 7,970,553 B2
(45) Date of Patent: Jun. 28, 2011

(54) CONCURRENT OPTIMIZATION IN SELECTION OF PRIMER AND CAPTURE PROBE SETS FOR NUCLEIC ACID ANALYSIS

(75) Inventors: Michael Seul, Fanwood, NJ (US);
Tatiana Vener, Stirling, NJ (US);
Xiongwu Xia, Irvine, CA (US)

(73) Assignee: BioArray Solutions, Ltd., Warren, NJ (US)

( * ) Notice: Subject to any disclaimer, the term of this patent is extended or adjusted under 35 U.S.C. 154(b) by 0 days.

(21) Appl. No.: 12/502,725

(22) Filed: Jul. 14, 2009

(65) Prior Publication Data
US 2010/0021909 A1    Jan. 28, 2010

Related U.S. Application Data

(62) Division of application No. 10/892,514, filed on Jul. 15, 2004, now Pat. No. 7,574,305.

(60) Provisional application No. 60/487,451, filed on Jul. 15, 2003.

(51) Int. Cl.
*G01N 33/48* (2006.01)
(52) U.S. Cl. .......................... 702/20

(58) Field of Classification Search .............. 702/19
See application file for complete search history.

(56) References Cited

U.S. PATENT DOCUMENTS

| 2003/0077607 A1 | 4/2003 | Hopfinger et al. |
| 2003/0134326 A1 | 7/2003 | Hansen et al. |

*Primary Examiner* — Jerry Lin
(74) *Attorney, Agent, or Firm* — Womble Carlyle Sandridge & Rice, PLLC

(57) ABSTRACT

Disclosed is a method of iteratively optimizing two (or more) interrelated sets of probes for the multi-step analysis of sets of designated sequences, each such sequence requiring, for conversion, at least one conversion probe ("primer"), and each converted sequence requiring, for detection, at least one capture probe. The iterative method disclosed herein for the concurrent optimization of primer and probe selection invokes fast logical string matching functions to perform a complete cross-correlation of probe sequences and target sequences. The score function assigns to each probe-target alignment a "degree of matching" score on the basis of position-weighted Hamming distance functions introduced herein. Pairs of probes in the final selection may differ in several positions, while other pairs of probes may differ in only a single position. Not all such positions are of equal importance, and a score function is introduced, reflecting the position of the mismatch within the probe sequence.

10 Claims, 18 Drawing Sheets

Fig. 1A  End-weighted Hamming distance function, α=0.05, 0.1, 0.3
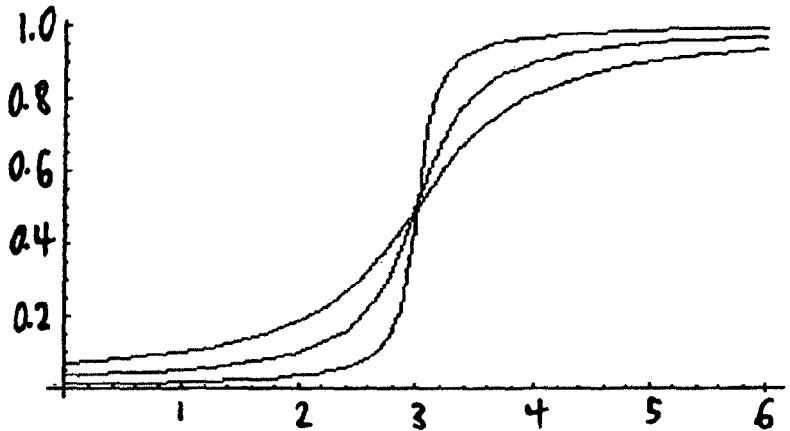
Fig. 1B  End-weighted Hamming distance function, δ=6, 8, 10
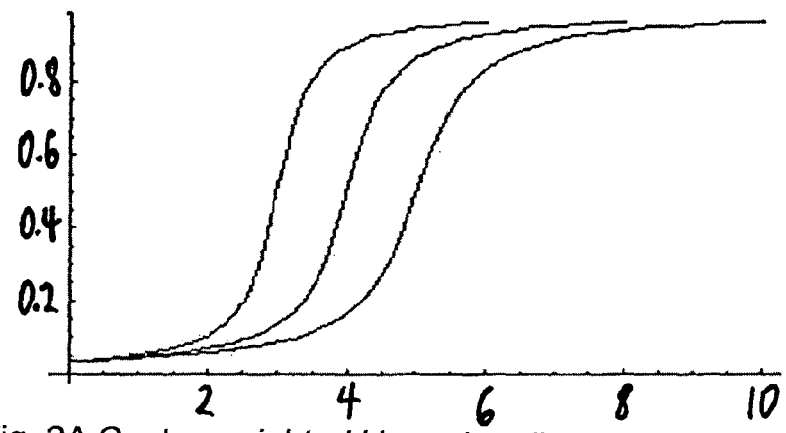
Fig. 2A Center-weighted Hamming distance function, α=0.05, 0.1, 0.3
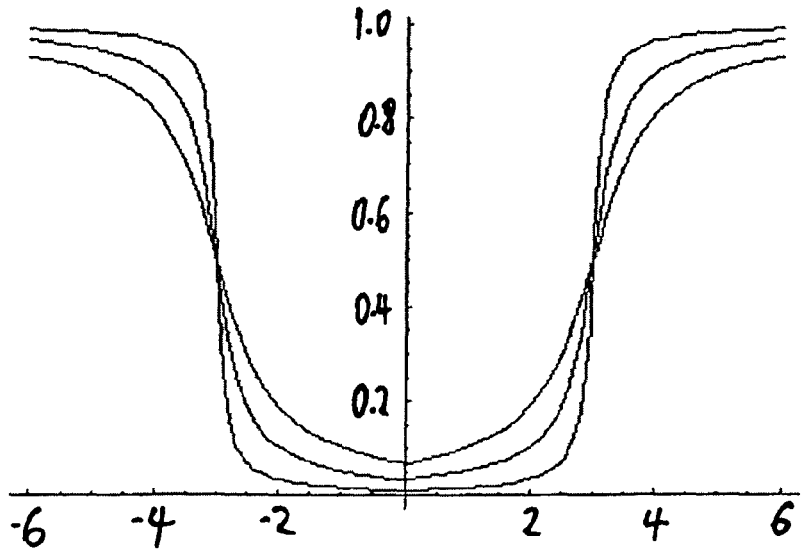

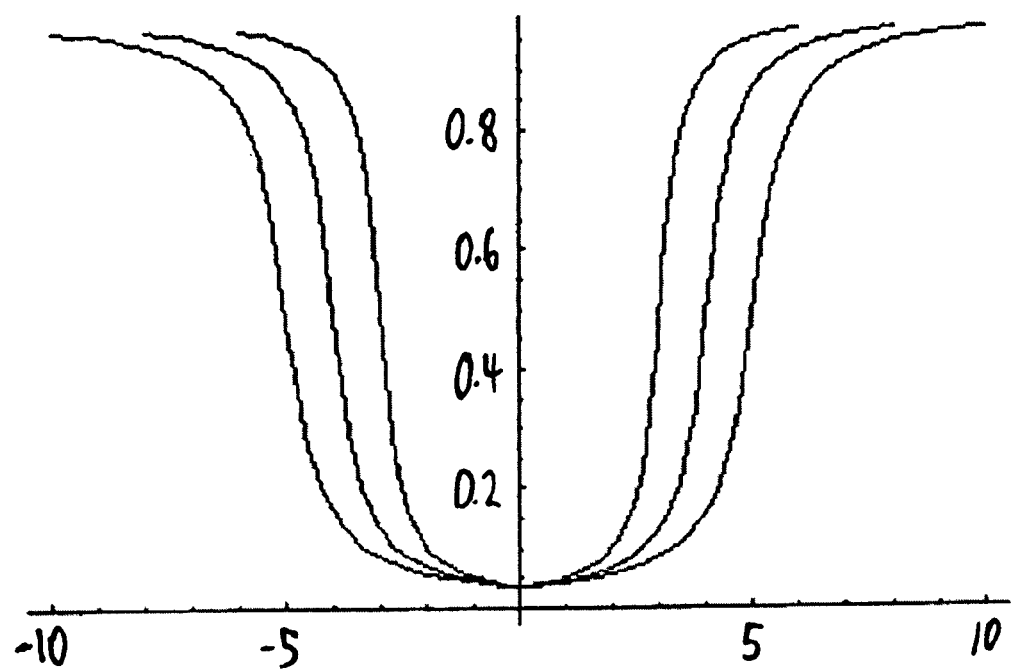
Fig. 2B Center-weighted Hamming distance function, δ=6, 8, 10

*Figure 4A*

(Interaction Matrix using 16 fmoles of Directly Labeled cDNA; Diagonals are Highlighted)

| RT Target Clean CTRL | IL-2, T RNA1 | IL-4, T RNA2 | IL-6, NTC RNA3, NT | IL-8, T RNA4 | IL-10, T RNA5 | TNF, T RNA6 | UBB, T RNA7 | GAPDH, T RNA8 | IFN, T RNA9 |
|---|---|---|---|---|---|---|---|---|---|
| prb1 | 612.764 | -33.5947 | -28.7036 | -20.6407 | | -33.5618 | -19.9596 | -42.4691 | -11.5546 |
| prb2 | 5.3019 | 428.522 | -37.3538 | -24.9513 | | -37.8343 | -29.8092 | -47.693 | -18.9246 |
| prb3 | -2.51903 | -42.3463 | -26.0832 | -37.1174 | | -41.9891 | -26.1189 | -50.2588 | -13.0368 |
| prb4 | 11.1386 | -29.3941 | -22.0914 | 1650.5 | | -24.8814 | -12.1328 | -33.8892 | -3.0462 |
| prb5 | 502.461 | 2223.63 | 1907.31 | 249.975 | failed | -38.9322 | -32.3685 | 3652.69 | 1200.89 |
| prb6 | -42.816 | -81.1404 | -63.2595 | -70.2281 | | 17.8711 | -63.8547 | -83.6158 | -53.8721 |
| prb7 | -36.0637 | -78.6969 | -70.9097 | -65.6203 | | -72.9756 | 27.1521 | -90.9599 | -49.9119 |
| prb8 | -42.3843 | -80.7007 | -72.5019 | -81.0955 | | -74.8708 | -56.9534 | -30.3883 | -52.9549 |
| prb9 | 14.1848 | -67.5992 | -72.4879 | -62.6141 | | -75.7374 | -62.8909 | -82.8712 | 705.399 |
| *Prb10* | -42.9123 | -90.1037 | -82.5149 | -69.9844 | | -88.8909 | -73.9923 | -95.8577 | -60.5344 |
| *Prb11* | -51.2778 | -91.1941 | -73.3929 | -90.2347 | | -85.0554 | -75.3599 | -96.8273 | -59.3868 |

*Figure 4B* (Interaction Matrix using cDNAs generated by designated primers)

| RT Primer | RT1 | RT2 | RT3 | RT4 | RT5 | RT6 | RT7 | RT8 | RT9 |
|---|---|---|---|---|---|---|---|---|---|
| Background | RNA1-9 | RNA1-9 | RNA1-9 | RNA1-9 | RNA1-9 | RNA1-9 | RNA1-9 | RNA1-9 | RNA1-9 |
| prb1 | 199.404 | 179.842 | 341.878 | 442.807 | 201.523 | 255.313 | 143.069 | 218.122 | 154.251 |
| prb2 | 169.659 | 412.401 | 165.588 | 211.58 | 119.597 | 180.921 | 124.566 | 214.945 | 139.403 |
| prb3 | 171.555 | 103.409 | 114.967 | 108.509 | 45.7253 | 138.835 | 95.2161 | 143.376 | 104.532 |
| prb4 | 190.216 | 125.934 | 157.482 | 1497.5 | 121.304 | 170.663 | 118.507 | 179.304 | 139.819 |
| prb5 | 165.87 | 118.955 | 117.154 | 318.52 | 91.807 | 156.708 | 97.8995 | 155.685 | 108.602 |
| prb6 | 128.644 | 42.3217 | 99.4871 | 92.3952 | 18.3902 | 237.869 | 32.0034 | 121.577 | 51.1943 |
| prb7 | 147.29 | 107.098 | 144.061 | 140.872 | 105.983 | 172.63 | 144.744 | 152.47 | 93.1961 |
| prb8 | 133.862 | 46.0439 | 106.496 | 96.0631 | 26.5329 | 126.051 | 44.7626 | 150.008 | 51.1739 |
| prb9 | 167.869 | 154.955 | 177.652 | 166.779 | 117.329 | 180.869 | 103.427 | 163.52 | 713.946 |
| *Prb10* | 126.005 | 45.7716 | 53.2636 | 89.1725 | 2.86093 | 111.163 | 21.073 | 117.311 | 43.145 |
| *Prb11* | 122.377 | 34.0917 | 52.0946 | 42.877 | -2.41865 | 115.319 | 23.552 | 117.256 | 46.4016 |
| | | | | | | | | | |
| Mutiplex Signal | 776.598 | 649.085 | 157.791 | 1060.66 | 319.66 | 184.012 | 338.49 | 181.392 | 688.621 |
| Mutiplex S/N | 6.4 | 5.3 | 1.3 | 8.7 | 2.6 | 1.5 | 2.8 | 1.5 | 5.6 |

Fig. 4C

| Name | Assay Mean | Assay STD | Bead Count | S/N |
|---|---|---|---|---|
| IL-2, T | 571.054 | 85.1942 | 334 | 6.3 |
| IL-4, T | 447.451 | 52.5824 | 307 | 5.0 |
| IL-6, NTC | 147.158 | 24.962 | 354 | 1.6 |
| IL-8, T | 406.233 | 53.1921 | 343 | 4.5 |
| IL-10, T | 350.441 | 60.4026 | 330 | 3.9 |
| TNF, T | 526.273 | 64.1027 | 352 | 5.8 |
| UBB, T | 443.935 | 61.0365 | 403 | 4.9 |
| GAPDH, T | 321.86 | 40.2823 | 346 | 3.6 |
| IFN, T | 552.443 | 77.6868 | 360 | 6.1 |
| Oligo18, MM CTRL, T | 90.2682 | 18.3965 | 269 | 1.0 |
| anamycin (Neg CTRL), | 90.2312 | 20.0552 | 284 | 1.0 |

*Figure 5A*
(Interaction Matrix using 16 fmoles of Directly Labeled cDNA; Design rules applied for probes and primers; Diagonals are Highlighted)

| RT Target | IL-2, T | IL-4, T | IL-6, NTC | IL-8, T | IL-10, T | TNF, T | UBB, T | GAPDH, | IFN, T |
|---|---|---|---|---|---|---|---|---|---|
| Clean CTRL | RT1 | RT2 | RT3 | RT4 | RT5 | RT6 | RT7 | RT8 | RT9 |
| prb1 | 336.61 | 82.55 | 77.64 | 80.49 | 97.68 | 93.93 | 90.20 | 64.17 | 86.26 |
| prb2 | 146.98 | 222.67 | 74.44 | 76.42 | 97.30 | 90.40 | 86.32 | 59.09 | 82.20 |
| prb3 | 81.85 | 84.90 | 78.66 | 81.59 | 98.94 | 94.67 | 89.00 | 60.18 | 88.85 |
| prb4 | 88.65 | 91.14 | 84.22 | 300.44 | 103.73 | 100.35 | 97.16 | 65.23 | 93.72 |
| prb5 | 87.58 | 85.33 | 78.65 | 104.38 | 22.52 | 93.99 | 90.91 | 66.13 | 88.65 |
| prb6 | 51.15 | 50.18 | 36.45 | 48.91 | 59.44 | 228.58 | 53.25 | 16.55 | 52.89 |
| prb7 | 50.89 | 53.00 | 37.69 | 47.35 | 57.98 | 62.22 | 298.28 | 19.32 | 53.86 |
| prb8 | 53.99 | 49.45 | 51.31 | 47.64 | 59.07 | 59.20 | 51.23 | 205.05 | 52.70 |
| prb9 | 59.96 | 54.56 | 48.28 | 48.42 | 61.94 | 61.10 | 54.89 | 20.01 | 549.50 |
| *Prb10* | 33.17 | 32.66 | 25.43 | 30.50 | 43.04 | 53.60 | 34.65 | 3.95 | 33.80 |
| *Prb11* | 32.53 | 34.52 | 28.62 | 32.16 | 46.12 | 53.67 | 34.98 | 5.30 | 35.06 |
| calibration | 3708.87 | 3758.90 | 3974.72 | 3900.97 | 3955.14 | 3934.72 | 4006.42 | 3795.87 | 3786.08 |

*Figure 5B*

(Interaction Matrix using cDNAs generated by designated primers;
Design rules applied for probes and primers; Diagonals are Highlighted)

| RT Primer | RT1 | RT2 | RT3 | RT4 | RT5 | RT6 | RT7 | RT8 | RT9 |
|---|---|---|---|---|---|---|---|---|---|
| Background | RNAI-9 | RNAI-9 | RNAI-9 | RNAI-9 | RNAI-9 | RNAI-9 | RNAI-9 | RNAI-9 | RNAI-9 |
| prb1 | 519.06 | 246.86 | 238.41 | 197.49 | 249.0 | 217.44 | 232.70 | 206.84 | 233.35 |
| prb2 | 269.75 | 331.26 | 210.87 | 175.64 | 209.0 | 180.92 | 197.57 | 176.08 | 209.99 |
| prb3 | 123.66 | 126.92 | 147.33 | 125.46 | 145.0 | 114.10 | 126.94 | 107.32 | 146.05 |
| prb4 | 139.60 | 147.23 | 169.90 | 180.00 | 181.9 | 141.12 | 146.20 | 132.99 | 165.23 |
| prb5 | 152.28 | 181.14 | 185.89 | 181.47 | 313.0 | 162.46 | 151.44 | 139.87 | 175.16 |
| prb6 | 146.45 | 175.38 | 177.48 | 148.87 | 191.0 | 476.97 | 151.13 | 149.12 | 185.40 |
| prb7 | 110.78 | 115.11 | 135.96 | 104.83 | 140.0 | 117.00 | 450.1 | 93.08 | 131.48 |
| prb8 | 99.42 | 112.44 | 124.09 | 91.42 | 128.0 | 93.64 | 88.62 | 265.35 | 114.00 |
| prb9 | 113.79 | 140.04 | 144.75 | 124.28 | 149.0 | 117.08 | 141.99 | 110.44 | 568.93 |
| *Prb10* | 85.39 | 70.35 | 97.93 | 71.91 | 103.0 | 63.70 | 71.91 | 60.04 | 86.79 |
| *Prb11* | 88.56 | 67.10 | 91.83 | 69.42 | 99.0 | 67.51 | 64.31 | 53.34 | 81.32 |
| calibration | 3928.68 | 3695.57 | 3965.38 | 4029.11 | 4125.0 | 3926.85 | 3890.80 | 3774.29 | 3812.82 |
| Mutiplex Signal | 571.05 | 447.45 | 147.16 | 406.23 | 350.44 | 526.27 | 443.94 | 321.86 | 552.44 |
| Mutiplex S/N | 6.3 | 5.0 | 1.6 | 4.5 | 3.9 | 5.8 | 4.9 | 3.6 | 6.1 |

Fig. 5C

| Name | Assay Mean | Assay_STD | Bead Count | S/N |
|---|---|---|---|---|
| IL-2, T | 776.598 | 111.456 | 296 | 6.4 |
| IL-4, T | 649.085 | 83.1802 | 294 | 5.3 |
| IL-6, NTG | 157.791 | 42.0825 | 323 | 1.3 |
| IL-8, T | 1060.66 | 141.907 | 315 | 8.7 |
| IL-10, T | 319.656 | 61.0099 | 298 | 2.6 |
| TNF, T | 184.012 | 46.1326 | 318 | 1.5 |
| UBB, T | 338.49 | 57.2532 | 308 | 2.8 |
| GAPDH, T | 181.392 | 39.5248 | 292 | 1.5 |
| IFN, T | 688.621 | 81.5937 | 273 | 5.6 |
| Oligo18, MM GTRL, T | 128.051 | 32.1891 | 292 | 1.1 |
| Kanamycin (Neg GTRL), T | 115.711 | 35.6071 | 257 | 0.9 |

Fig. 6

| POSITION | SEQUENCE | PRIMER-NAME | PRIMER | SIGNAL |
|---|---|---|---|---|

NM_152899 (SP1056-A03 – entire clone), IL-4

| | | | | |
|---|---|---|---|---|
| 67 | CCCTGCACCTCCTCGTCC | IL-4 | ACCTCCTCGTCCTCGTCC | 37.7317 |
| 73 | ACCTCCTCGTCCTCGTCC | IL-4 | ACCTCCTCGTCCTCGTCC | 0 |
| 79 | TCGTCCTCGTCCCCATCC | IL-4 | ACCTCCTCGTCCTCGTCC | 40.3649 |

NM_000565 (BM1155_G10 – ORF) IL-6

| | | | | |
|---|---|---|---|---|
| 123 | GCCCGGTTCCCATTAGC | IL-6 | GCCCGGTTCCCATTAGC | 0 |
| 1104 | GCCCGGAGGCCATGGGC | IL-6 | GCCCGGTTCCCATTAGC | 5.0326 |

NM_001558 – (PL1231_H12 – ORF) IL-10

| | | | | |
|---|---|---|---|---|
| 95 | TCTTGGCTCAGACGCTCAT | IL-10 | TCTTGGCTCAGACGCTCAT | 0 |

NM_018955 (PL1104_C12 – clone) UBB

| | | | | |
|---|---|---|---|---|
| 67 | AACCCTTACCGGCAAGAC | UBB | AACCCTTACCGGCAAGAC | 0 |
| 295 | GACCCTGACCGGCAAGAC | UBB | AACCCTTACCGGCAAGAC | 29.6179 |
| 523 | GACCCTGACCGGCAAGAC | UBB | AACCCTTACCGGCAAGAC | 29.6179 |

NM_002046 (AB1001_E06 – clone) GAPDH

| | | | | |
|---|---|---|---|---|
| 219 | GCAAATTCCATGGCACCGTCA | GAPDH | GCAAATTCCATGGCACCGTCA | 0 |

NM_000416 (AB3265_F11 – clone) INF

| | | | | |
|---|---|---|---|---|
| 96 | CCGTCCTCAGTGCCTACAC | IFN | CCGTCCTCAGTGCCTACAC | 0 |

Fig. 6 (Con't)

```
POSITION  SEQUENCE              PRIMER-NAME    PRIMER                SIGNAL
NM_000206 (BM1296-A11) , IL-2 - complete sequence (pCMV6-XL4 vector)
77  CGACAATTCTGACGCCCAATG       IL-2           CGACAATTCTGACGCCCAATG  0

NM_001066 (BC1333_C09), TNF - complete sequence (pCMV6-XL5 vector)
682 GTCTGCACGTCCACGTCC          IL-4           ACCTCCTCGTCCTCGTCC    50.837
688 ACGTCCACGTCCCCCACC          IL-4           ACCTCCTCGTCCTCGTCC    13.8196
207 CCGGCTCAGAGAATACTATGA       TNF            CCGGCTCAGAGAATACTATGA  0

NM_000584 (BC1189_H09) , IL-8 - ORF (pCMV6-XL5 vector)
146 TTTGCCAAGGAGTGCTAAAGA       IL-8           TTTGCCAAGGAGTGCTAAAGA  0
```

Fig. 7

| POSITION | SEQUENCE | PROBE_NAME | PROBE | SIGNAL |
|---|---|---|---|---|
| NM_152899 (SP1056-A03 - entire clone) IL-4 | | | | |
| 6 | TGTCCTGCTGTCACCAAGAG | IL-4 | TGTCCTGCTGTCACCAAGAG | 0 |
| NM_000565 (BM1155_G10 - ORF) | | IL-6 | | |
| 22 | CAGTGTGTGTAGAGAGCCGG | IL-6 | CAGTGTGTGTAGAGAGCCGG | 0 |
| NM_001558 - (PL1231_H12 - ORF) IL-10 | | | | |
| 48 | ATGCTGCCGTGCCTCGTAG | IL-10 | ATGCTGCCGTGCCTCGTAG | 0 |
| N_018955 (PL1104_C12 - clone), UBB | | | | |
| 19 | GCAGGATCCTGGTATCCGCTA | UBB | GCAGGATCCTGGTATCCGCTA | 0 |
| NM_002046 (AB1001_E06 - clone) GAPDH | | | | |
| 77 | GGAGTCAACGGATTTGGTCGT | GAPDH | GGAGTCAACGGATTTGGTCGT | 0 |
| NM_000416 (AB3365_F11 - clone) INF | | | | |
| 35 | TCTCCTACCCCTTGTCATGC | IFN | TCTCCTACCCCTTGTCATGC | 0 |
| NM_000206 (BM1296-A11), IL-2 - complete sequence (pCMv6-XL4 vector) | | | | |
| 6 | GTTGAAGCCATCATTACCATTCACA | IL-2 | GTTGAAGCCATCATTACCATTCACA | 0 |
| NM_001066 (BC1333_C09), TNF - complete sequence (pCMv6-XL5 vector) | | | | |
| 163 | CAGGTGGCATTTACACCCTACG | TNF | CAGGTGGCATTTACACCCTACG | 0 |
| NM_000584 (BC1189_H09), IL-8 - ORF (pCMv6-XL5 vector) | | | | |
| 2 | GCAGAGCACACAAGCTTCTAGG | IL-8 | GCAGAGCACACAAGCTTCTAGG | 0 |

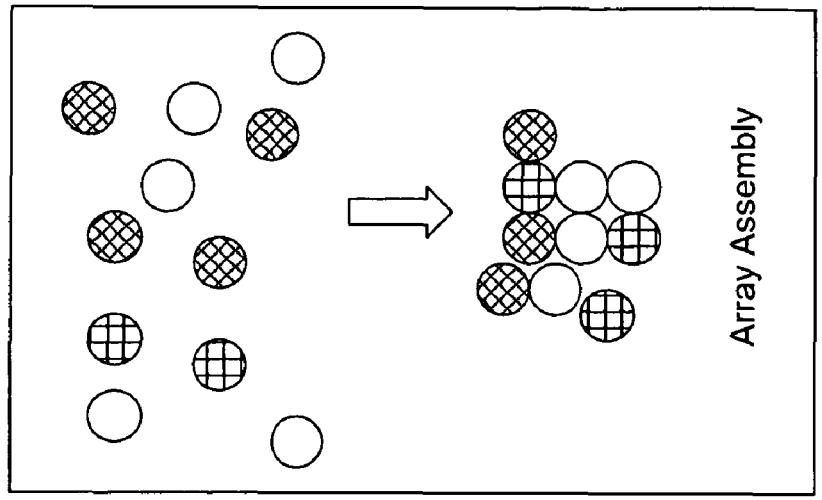
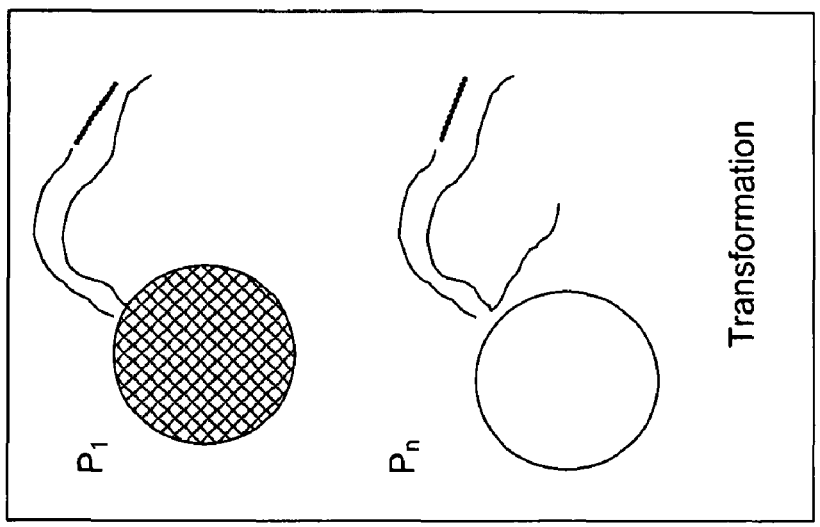
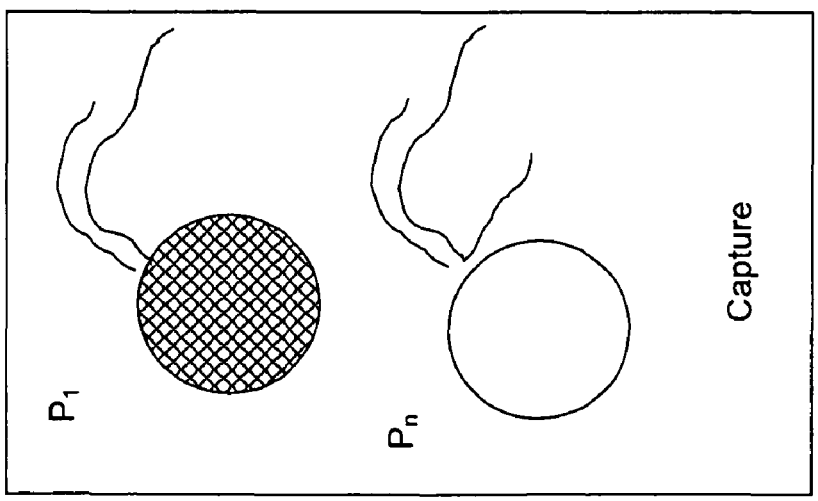
Fig. 13

CONCURRENT OPTIMIZATION IN SELECTION OF PRIMER AND CAPTURE PROBE SETS FOR NUCLEIC ACID ANALYSIS

RELATED APPLICATIONS

This application is a divisional of U.S. application Ser. No. 10/892,514 filed Jul. 15, 2004, now U.S. Pat. No. 7,574,305 and claims priority to it and to U.S. Provisional Application No. 60/487,451, filed Jul. 15, 2003.

BACKGROUND

Parallel assay formats permitting the concurrent ("multiplexed") analysis of multiple analytes in a single reaction are gaining wide-spread acceptance in the analysis of proteins and nucleic acids in molecular medicine and biomedical research. Multiplexed formats of nucleic acid analysis—either in solution or in a solid phase format involving arrays of immobilized primers and probes (see, e.g., U. Maskos, E. M. Southern, *Nucleic Acids Res.* 20, 1679-1684 (1992); S. P. A. Fodor, et al., *Science* 251, 767-773 (1991))—generally involve the selection of oligonucleotide probes whose specific interaction with designated subsequences within a given set of target sequences of interest reveals the composition of the target at the designated position(s).

Applications of particular practical interest, involve multistep procedures, such as, as a first step, the conversion of a set of original sequences into a selected subset, for example by means of amplification of selected subsequences of genomic DNA by PCR amplification to produce corresponding amplicons, or by means of reverse transcription of selected subsequences of mRNA to produce corresponding cDNAs. In the simplest such sequence of process steps, a conversion step is followed by a detection step to complete the analysis. In these applications, the reliability of multiplexed nucleic acid analysis critically depends on the specific and preferably exclusive interaction of primers with their respective cognate target subsequences and the specific and preferably exclusive interaction of probes with their respective cognate subsequences within the targets produced in the conversion step. Accordingly, described herein are methods which, given a set of target sequences of interest, allow selection of conversion probes ("primers") and detection probes so as to minimize the interaction of a given primer or probe with any but its cognate target subsequence.

Multiplexed Expression Profiling—Methods of gene expression analysis have been widely used in connection with target discovery or mapping, in which genes of interest may not be known a priori and a significant risk of error may have to be tolerated. Conversely, in diagnostic applications involving a designated set of genes of interest, the multiple sources of potential error inherent in the aforementioned approaches generally will not be tolerable. The present invention discloses methods of analysis suitable for diagnostic applications as well as target validation and patient profiling.

Known methods for multiplexed expression analysis use either randomly placed short reverse transcription (RT) primers to convert a set of RNAs into a heterogeneous population of cDNAs, or a universal RT primer directed against the polyA tail of the mRNA to produce full-length cDNAs. While these methods obviate the need for design of sequence-specific RT primers, both have significant disadvantages in quantitative expression monitoring, which requires the quantitative determination of cDNA levels in the target mixture as a measure of the levels of expression of the corresponding mRNAs.

The determination of gene expression levels may be performed in a parallel format by employing an array of oligonucleotide capture probes or, in some cases, cDNA molecules disposed on a planar substrate, and contacting the array—under specific conditions permitting formation of probe-target complexes—with a solution containing nucleic acid samples of interest, including mRNAs extracted from a particular tissue, or cDNAs produced from the mRNAs by reverse transcription (RT). Following completion of the complex formation ("hybridization") step, unbound target molecules are removed, and intensities are recorded from each position within the array, these intensities reflecting the amount of individual probe-target complexes formed during the assay. This pattern is analyzed to obtain information regarding the abundance of mRNAs expressed in the sample.

In a commonly practiced approach to multiplexed expression profiling, mRNA molecules in a sample of interest are first reverse transcribed to produce corresponding cDNAs and are then contacted with an array of oligonucleotide capture probes formed by spotting or by in-situ synthesis. Lockhart et al., U.S. Pat. No. 6,410,229 invoke a complex protocol to produce cRNA, wherein mRNA is reverse transcribed to cDNA, which is in turn transcribed to cRNA under heavy labeling—of one in eight dNTPs on average—and detected on an array of synthesized oligonucleotide probes using a secondary "decoration" step. This is a complex, lengthy and expensive process.

These known methods rely on multiplexed probe-target hybridization, which is known to be lacking in specificity, as the single step of sequence-specific discrimination between, and quantitative determination of, multiple target sequences. Randomly placed RT primers will produce a representative population of cDNAs; that is, one in which each cDNA is represented with equal frequency, only in the limit of infinitely long mRNA molecules. The analysis of a designated set of short mRNAs by random priming generally will produce cDNAs of widely varying lengths for each type of mRNA in the mixture, and this in turn will introduce potentially significant bias in the quantitative determination of cDNA concentration, given that short cDNAs will more readily anneal to immobilized capture probes than will long cDNAs. Further, the production of full-length cDNAs, if in fact full-length RT is successful, provides a large sequence space for potential cross-reactivity between probes and primers, making the results inherently difficult to interpret and unreliable.

Some methods of multiplexed hybridization use long probes in spotted arrays. Note that Agilent EP 1207209 discloses probes of preferred length 10 to 30 nucleotides, and preferably about 25 nucleotides. These may offer an advantage—in the generally undesirable situation in which probe adhesion to the substrate randomly obstructs target access to probe sequences of interest because probe-target complex formation generally will not involve the full length, but rather randomly accessible subsequences of the probe. However, in a long probe, the probe sequence of interest may be obstructed and not accessible.

Differential Gene Expression—Gene expression analysis has been widely used to characterize molecular differences between normal tissue or cells vs diseased or otherwise altered tissue or cells, or differences between normal ("wild-type") vs transgenic plants. In accordance with a commonly practiced approach to differential gene expression, a set of cDNA clones is "spotted" onto a planar substrate to form the probe array which is then contacted with DNA produced from normal and altered sources, the two types of DNA. DNA from the two sources is differentially labeled to permit the recording of patterns formed by probe-target hybridization in two color channels and thus permitting the determination of expression ratios in normal and altered samples (see, e.g., U.S. Pat. No. 6,110,426 (Stanford University)). The system of two-color fluorescent detection is cumbersome and may lead to errors of detection.

Multiplexed Analysis of Mutations and Polymorphisms—Another well-known method for multiplexed conversion of genomic DNA sequences to a selected set of short DNA subsequences is amplification with sequence-specific primers, as in the example of linear amplification by strand displacement or other methods or geometric amplification by PCR. Following amplification, the amplicons can be analyzed by hybridization detection or by hybridization coupled with elongation detection, using cognate probes. Selection of primers and probes can avoid excessive cross-hybridization and enhance the reliability of the results. The methods described herein also relate to applications that call for amplification followed by detection, as well as to situations calling for the concatenation of multiple conversion and detection steps.

What is desirable in these applications is the selection, for each target, of a matching ("cognate") probe, that is, a probe with a sequence that is perfectly complementary to one and only one designated subsequence while containing at least one, but preferably several non-complementary ("mismatched") positions with respect to all other sequences (or subsequences on the same target strand as the cognate subsequence) in the reaction (see e.g., "Selection of optimal DNA oligos for gene expression arrays", Li & Stormo, Bioinformatics 17, 1067-1076 (2001)). To select one among several possible candidate probes, known methods rely on the evaluation of sequence-dependent free energies of the complex ("duplex") formed between primer or probe and target, the analysis culminating in the evaluation of the thermodynamic stability of the complex in terms of a "melting" temperature (Cantor & Smith, "Genomics", 2001).

Several available algorithms for primer and probe design have been described which invoke NN-interaction parameters to compute the free energy of a hybridization complex of known sequence whose thermodynamic stability is expressed in the form of a "melting temperature", $T_m$; at $T=T_m$, half of the complex has denatured into its constituent strands. Several commercially available software packages focus on the detailed modeling of probe-target interaction under a wide range of relevant experimental parameters to predict the stability of the complex as well as competing structures such as folded target or probe strands, the latter including certain hairpin configurations. In the majority of commercial primer or probe design tools, the issue of cross-reactivity, critical to the design of multiplexed assays, remains substantially unaddressed.

When sequence homologies are taken into account, this is achieved by pairwise comparison using standard search tools such as BLAST (see, e.g., PrimerSelect (DNAStar), ArrayDesigner 2(Premier Biosoft)), an approach that not only requires significant time and effort in manually performing pairwise comparisons by "cutting and pasting", but also fails for long templates (>1 kb), and generally ignores the fact that the position of a mismatch within the primer or probe sequence plays a critical role in determining the actual extent of cross-reactivity. Moreover, the design of conversion probes ("primers") is treated independently of the design of detection probes, creating a source of unreliability.

Design of Unique Sequences: Coding—The issue of selecting a set of unique probe sequences is central to the design of DNA codes, namely sets of equi-length "words" composed of the letters A, T, G and C, for purposes of designing methods of parallel sequencing, storing ("encoding") information in chemical libraries such as "zip code" oligos (U.S. Pat. No. 5,981,176 to Wallace) or analog ("DNA") computing. The objective of code design is to find a set of N-letter words (herein also referred to as "N-strings") wherein any two words differ in at least d positions with respect to the Watson-Crick base pairing rules—that is, words have a Hamming distance of at least d # N. Generally, codes satisfy additional constraints, for example, the constraint that free energies, computed on the basis of standard nearest-neighbor (NN) interaction parameters (Cantor & Smith, "Genomics", 2001), fall into a given range.

The methods herein address a different situation: probe sequences must be identified which match a preselected set of target sequences while minimizing unwanted cross-reactions with other than the cognate sequences. In view of the foregoing considerations, it will be desirable, for diagnostic application of gene expression analysis—herein also referred to as multiplexed expression monitoring (mEM)—as well as for related situations involving target amplification—to have flexible and rapid methods by which to produce correlated sets of desirable conversion probes such as RT primers and detection probes such as probes for hybridization-mediated target capture which enhance the level of reliability.

SUMMARY

Disclosed is a method of iteratively optimizing two (or more) interrelated sets of probes for the multi-step analysis of sets of designated sequences, each such sequence requiring, for conversion, at least one conversion probe ("primer"), and each converted sequence requiring, for detection, at least one capture probe. The iterative method disclosed herein for the concurrent optimization of primer and probe selection invokes fast logical string matching functions to perform a complete cross-correlation of probe sequences and target sequences. The score function assigns to each probe-target alignment a "degree of matching" score on the basis of position-weighted Hamming distance functions introduced herein. Pairs of probes in the final selection may differ in several positions, while other pairs of probes may differ in only a single position. Not all such positions are of equal importance, and a score function is introduced, reflecting the position of the mismatch within the probe sequence.

These methods can be used for multiplexed expression monitoring of a designated set of genes by way of multi-tiered, sequence-specific discrimination at the level of sequence conversion, specifically reverse transcription, as well as sequence detection, specifically hybridization-mediated sequence-specific capture, optionally followed by sequence-specific, target-mediated probe elongation. The methods herein also relate to the design of probe sets for multiplexed analysis including more than two steps, such as amplification following reverse transcription or detection by means of probe elongation following capture. See U.S. Pat. No. 4,851,331 by Vary et al. In another aspect, used in analysis of double stranded DNA rather than in expression monitoring, the method may include a further step of selecting probes hybridizing to either sense or anti-sense targets produced by a PCR of double stranded DNA, and additional PCR reactions, according to specified design rules.

In one example of a specific application of the foregoing methods, they can be used to design an assay system for detecting the presence of particular nucleic acid (DNA or RNA) sequences in a sample, or the presence of the reverse transcriptase enzyme itself (thereby indicating the presence of retrovirus in the sample) using improvements over a known system for transcription amplification, as described in U.S. Pat. No. 5,399,491; Guatelli et al., Proc. Nat's Acad. Sci. USA, 87: 1874-78 (1990) (both being incorporated by reference). In such an assay system, a homogeneous reaction protocol integrates such a nucleic acid (DNA or RNA) amplification method with enzyme-mediated, multiplexed analysis, preferably by way of capture-mediated elongation detection. Microparticles, with elongation probes attached, may be employed for the sequence-specific capture and elongation of selected RNA or genomic DNA subsequences, as described, for example, in U.S. Pat. No. 4,851,331 and in International Application No. WO/03034029. The sample for the nucleic acids may be a cell lysate or another source. Following elongation, the microparticles may be captured to other microbeads, and detected, in accordance with the methods and formats disclosed in International Application No. WO/03058196, preferably by real-time array assembly. This functionally integrated sequence of reaction steps, performed in a homogeneous manner, that is, without intervening separation or washing steps, can also be miniaturized. See International Application No. WO/03058196.

The invention will now be described in further detail with reference to the drawings.

BRIEF DESCRIPTION OF THE DRAWINGS

FIG. 1a—End-weighted Hamming distance function for three values of parameter α, representing the steepness of the probe-target mismatch penalty.

FIG. 1b—End-weighted Hamming distance function for three values of parameter δ, which represents the probe-target mismatch penalty.

FIG. 2a—Center-weighted Hamming distance function for three values of parameter α, representing the steepness of the probe-target mismatch penalty.

FIG. 2b—Center-weighted Hamming distance function for three values of parameter δ, which represents the probe-target mismatch penalty.

FIG. 4A—Interaction matrix for nine probes (and two controls) with their individual respective targets, where the targets are generated by RT primers from the RT targets shown, the probes and primers having been selected without optimization in accordance with the methods of the invention.

FIG. 4B—Plot of the interaction between the probes and targets as in 4A, but where the elongation products generated by each RT primer against all RT Primer targets are placed in the reaction mixture with the probes.

FIG. 4C—Shows the assay mean signal, standard deviation, bead count and signal/noise ratio for the assay of FIG. 4A.

FIG. 5A—Interaction matrix for nine probes (and two controls) with their individual respective targets, where the targets are generated by RT primers from the RT targets shown, the probes and primers having been selected without optimization in accordance with the methods of the invention.

FIG. 5B—Plot of the interaction between the probes and targets as in 5A, but where the elongation products generated by each RT primer against all RT Primer targets are placed in the reaction mixture with the probes.

FIG. 5C—Shows the assay mean signal, standard deviation, bead count and signal/noise ratio for the assay of FIG. 5A.

FIG. 6—Matrix showing the sequence of a several sets of conversion probes, each set homologous to a human cytokine. FIG. 6 discloses SEQ ID NOS 67-98, respectively, in order of appearance.

FIG. 7—Matrix showing the sequence of a several sets of detection probes, each set homologous to a human cytokine. FIG. 7 discloses SEQ ID NOS 99-116, respectively, in order of appearance.

FIG. 13—Depicts an array of microparticles with attached probes, which have been elongated, captured to magnetic microbeads and assembled into an array.

DETAILED DESCRIPTION

Figure 3:
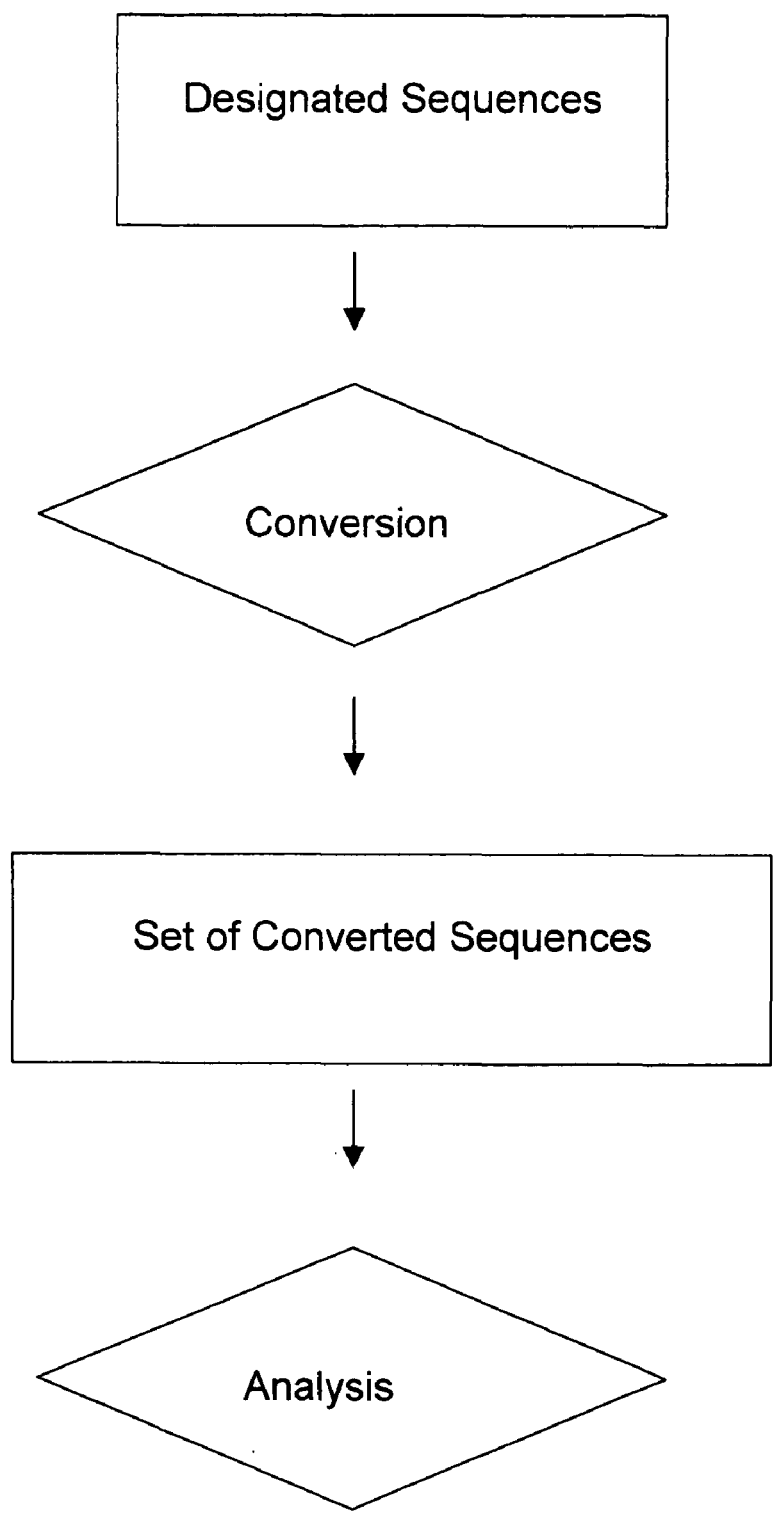
FIG. 3—Flow chart for "conversion"—"detection" sequence of multiplexed analysis
Figure 8:
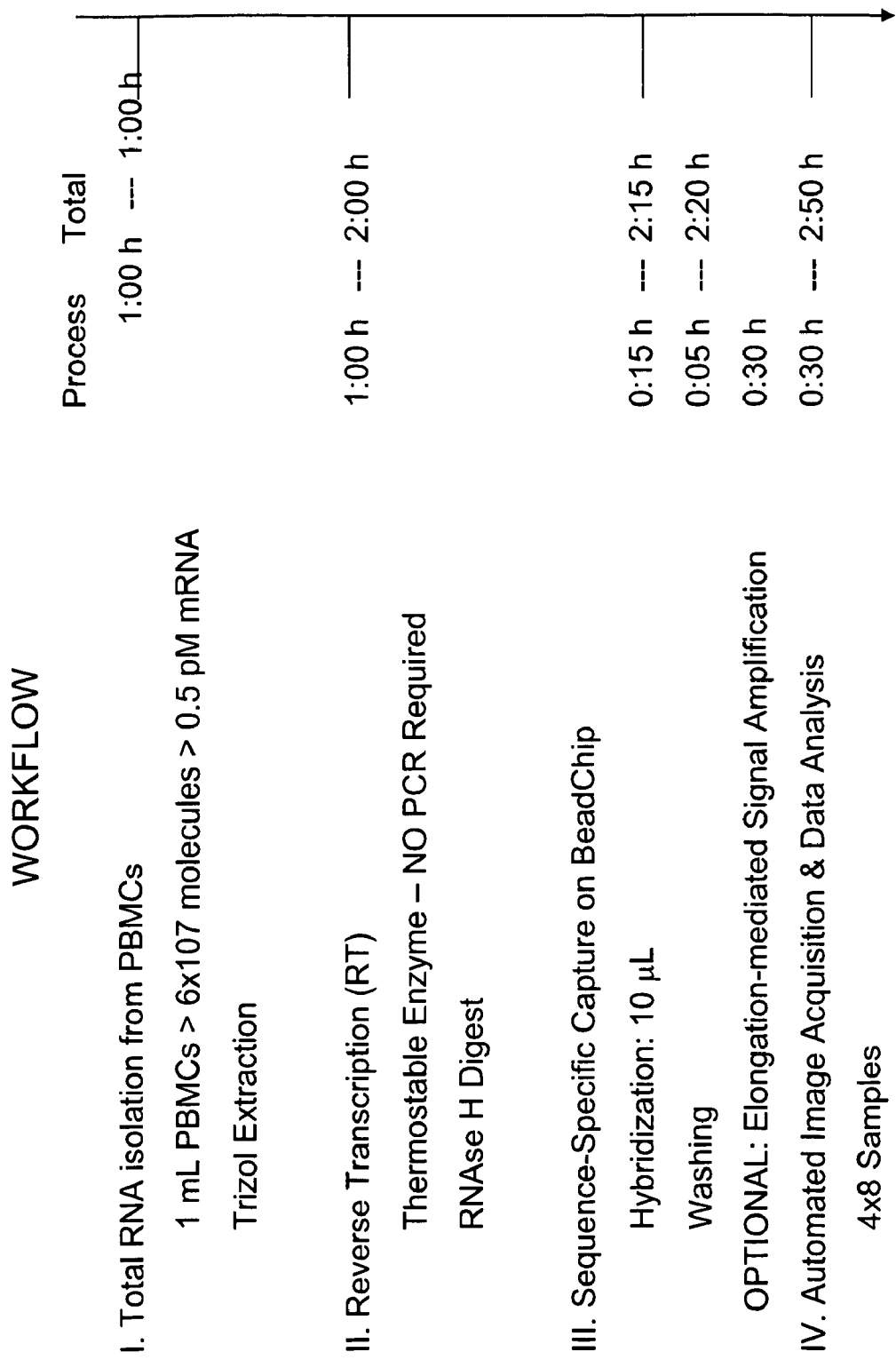
FIG. 8—Flowchart indicating the time involved in various steps of expression monitoring, in accordance with the methods described herein.

The invention discloses a method of concurrent optimization in selecting sequence-specific conversion probes so as to produce a desired set of converted (sub)sequences, and selecting detection probes for analysis of the converted sequences. For gene expression monitoring, the conversion probes will serve as RT primers to produce from the original set of designated mRNA sequences a set of cDNA sequences to be analyzed by a set of sequence-specific detection probes, for example by way of hybridization-mediated capture, or hybridization followed by elongation.

Concurrent optimization is attained by iterative approximate diagonalization of a first interaction matrix $\Gamma = (\gamma_{jk})_{j=1,M;\ k=1,N \leq M}$ governing the interaction between conversion probes such as RT primers, $\pi_j$, and a first set of sequences such as a set of mRNA targets, $T_k$, and diagonalization of a second interaction matrix, $C = (c_{ij})_{i=1,P;\ j=1,\ M \leq P}$, governing the interaction between capture probes, $p_i$, and converted sequences such as cDNA targets, $t_j$, produced by the j-th RT primer—or multiple such primers—by reverse transcription of the k-th mRNA. Disclosed are weighted Hamming distance functions to evaluate the interaction strengths which form the elements of the interaction matrices. Specifically, the interaction strengths, $\gamma_{jk}$, are evaluated, in all possible alignments of the j-th RT primer and k-th mRNA target, in terms of an end-weighted Hamming distance function, and the interaction strengths, $c_{ij}$, are evaluated, in all possible alignments of the i-th probe and j-th cDNA target, in terms of a center-weighted Hamming distance function.

The method proceeds by iterative variation of parameters relating to primers and corresponding probes, for example, iterative shifting of primer and probe positions as well as padding and pruning or change in base composition of primer and probe sequences, in such as way as to cause the evolution of both interaction matrices toward a diagonal form. This method of concurrent ("coupled") optimization is capable of accommodating constraints on the choice of primers and probes such as the preference for placement of RT primers so as to produce short cDNAs and the placement of probes in proximity to the 5'-end of the cognate cDNA or the choice of preferred operating temperature, T, and range of "melting" temperatures of primer-mRNA and probe-cDNA complexes, reflecting primarily the length and relative GC content of primers and probes.

An optimal first selection will favor the exclusive interaction of each primer in the set with only its designated ("cognate") target subsequence—and hence minimize the interaction of primers with non-cognate target subsequences—in order to mediate the conversion of selected segments of the designated target sequences into a set of converted target sequences. An optimal second selection will favor the exclusive interaction of each detection probe in the set with only its cognate subsequence within the set of converted target sequences—and hence minimize the interaction of probes with non-cognate target subsequences.

The method herein specifically relates to the concurrent optimization in selecting sequence-specific primers for multiplexed reverse transcription (RT) of a given set of mRNA molecules so as to produce a desired set of cDNAs of specified length, generally shorter than the length of the original mRNA sequence, and selecting probes for hybridization-mediated capture of said cDNAs. A parallel format of analysis involving the interrogation and quantitative determination of multiple nucleic acids in a single ("multiplexed") reaction has the advantage not only of high throughput but also of concurrent analysis of the expression levels of frequently interrelated genes. Given a designated set of genes to be analyzed, it will be advantageous to attain sequence-specificity at multiple tiers of analysis including reverse transcription and to select RT primers to produce a set of cDNAs, preferably of short length given that the quantitative full-length reverse transcription of long mRNAs and the quantitative capture of long cDNAs are problematic.

The methods herein take advantage of the a priori knowledge of the sequences and anticipated levels of abundance of the designated mRNAs of interest to select and place RT primers in specific regions of each mRNA in order to control the length and degree of labeling of the cDNA produced in the RT reaction. In some cases, it will be advantageous to place multiple RT primers on one or several of the mRNAs in the designated set and to analyze the corresponding cDNAs using multiple probes directed against different subsequences of these cDNAs. This is referred to herein as "Multiple Primer Multiple Probe" (mpmp) design. In some situations, it will be advantageous to perform the further step of amplifying the reverse transcripts prior to detection. The methods herein thus also relate to the concurrent selection of optimal amplification primers and detection probes for the multiplexed analysis of mutations and polymorphisms as discussed further below.

Also disclosed are methods for the selection of sequence-specific amplification primers for PCR of a given set of DNA sequences so as to produce a desired set of amplicons of specified length, generally shorter than the length of the original DNA sequence, and selecting probes for hybridization-mediated capture of said amplicons or other forms of analysis as disclosed in Provisional Patent Ser. No. 60/470,806, "Hybridization-Mediated Analysis of Polymorphisms (hMAP)," filed May 15, 2003.

Symmetric PCR—The methods herein relate to the design of sequence-specific PCR primers for amplification of one or more selected portions of double-stranded (ds) DNA. Standard "symmetric" designs will produce two types of converted target sequences, namely sense (S+) and anti-sense (S−) converted target sequences ("amplicons"), each of which may be analyzed by capture to a set of sequence-specific as well as orientation-selective detection probes. That is, two sets of nucleic acid sequences are concurrently subjected to conversion and detection. Accordingly, the methods described herein for the case of multiplexed expression profiling directly apply to the selection of S+ primers for conversion of selected subsequences into S+ amplicons to be captured to a corresponding set of S− detection probes; and conversely, to the selection of S− primers for conversion of selected subsequences into S− amplicons to be captured to a corresponding set of S+ detection probes.

In the most general case, two sets of interaction matrices, $\{\Gamma+, C-\}$ and $\{\Gamma-, C+\}$, are constructed to guide the selection. One additional step, to be included in the empirical design rules guiding the initial primer selection as further elaborated herein below is the exclusion of self-complementary S+ primer/S− primer pairs. When the detection step relates to mutation or polymorphism analysis, shifting of probes is possible only in a narrow range given the requirement that the probe be directed to the subsequence containing the mutation of polymorphism; however, probe modification by pruning or padding or change of composition is available.

Strand Selection—The existence of two complete sets of conversion probes producing two related sets of converted target sequences provides the additional design choice of selecting, for each S+/S− pair of such converted sequences, only one sequence for detection. Among multiple such pairs, the selection of the preferred strand orientation is again guided by considerations of minimizing cross-reactivity.

Strand selection follows the completion of several rounds of symmetric amplification and serves the purpose of producing in abundance one selected orientation of converted target. This is readily accomplished using one of several methods well known in the art including: the use of unequal amounts of forward and reverse primers including the special case of performing only a single pass of the reaction using sequence-specific primers of one orientation—this "copy" step is invoked, for example, to introduce labels into the final product of only one orientation; and the exonuclease-mediated digestion of one strand, selected by way of incorporation of phosphorylated primers.

A special case of strand selection of interest herein involves an instance of "asymmetric" PCR which calls for the design of sequence-specific PCR primers for use in a "copying" step. Such a step typically will be performed, using a set of forward or a set of reverse primers, all of which typically will be directed to specific subsequences located interior to an amplicon produced in a reaction using a pair of primers directed against conserved sequences flanking the region targeted by the sequence-specific primers. Examples of this scenario include the genotyping of loci within the Human Leukocyte Antigen (HLA) complex as well as viral and bacterial strain (sub)typing. In this instance, the initial primer selection may be relatively simple, while design complexity may become significant once the sequence-specific primers are to be selected. It will be readily recognized that the optimal selection of conversion probes of one orientation, and the selection of corresponding detection probes, represents a direct analog to the situation described herein in connection with multiplexed expression monitoring (see FIG. 3A).

Strand selection simplifies the interaction matrices—for example, certain conversion probe-target pairs will be eliminated from $\Gamma+$ and their respective complements included in form of the corresponding matrix elements in $\Gamma-$ and vice versa; and certain detection probe-converted target pairs will be eliminated from $C+$ and their respective complements included in form of the corresponding matrix elements in $C-$ and vice versa. This is apparent from the description of the method in pseudocode format ("Pseudocode I") below.

```
/*
** Function performing Iterative Reconfiguration of Multiplexed Reaction
** by Strand and Group Selection using Evaluation of Interaction Matrices
**
** Strand and Group Selection are Governed by a Cutoff Parameter, €,
** applied to Off-diagonal Interaction Matrix Elements
*/
OptimizeReactionConfiguration(P, T, TYPE, €,)    /* P: set of conversion probes (TYPE
=E); or
                                                    set of detection probes
(TYPE =C) */
                                                 /* T: set of targets */
                                                 /* €: cut-off parameter controlling
                                                    convergence*/
{
    SeparateSenseAndAntiSenseTargets( T, T+, T-);
    SeparateSenseAndAntiSenseProbes( P, P+, P-);
/*
** Construct Optimal Interaction Matrix
** using end-weighted Hamming distance function (TYPE = E) or
** using center-weighted Hamming distance function (TYPE = C)
** unless already available from previous part of program
**
** For ds targets, arbitrarily select P- to start
*/
    OptimalInteractionMatrix( M, P-, T+, TYPE );    /* use function equivalent to
                                                       main ( ) above */
/* Stand Selection */
    FOR( all rows in M containing probes p- in P- )
    {
        FOR( all cols in M containing targets t+ in T+)
        {
            IF( (p- NOT cognate to t+) AND ( M(p-, t+) > € ) )
            {
                FlipOrientation (p-, fp-);
/*flipprobeorientation*/
/* r o w s of "complementary" matrix cM hold p+, cols of cM hold t- */
                ReplaceRow (p+ in cM by fp-);
                ReplaceRow (p- in M by 0);
                FlipOrientation (t+[p-], ft+[p-]);  /* flip orientation of
                                                       target cognate to p- */
                ReplaceCol (t- in cM by ft+[p-]);
                ReplaceCol (t+[p-] in M by 0);
            }
        }
    }
/* Eliminate all non-replaced probe and target sequences in "complementary" matrix
cM */
FOR( all rows in cM )
    FOR( all cols in cM)
    {
        IF( ( p+ NOT a flipped probe sequence )
        {
            ReplaceRow (p+ in cM by 0 );
            ReplaceCol (t- [p+] in cM by 0);
        }
    }
}
 /** Construct Optimal Interaction Matrix for Set of "Flipped" Probes and Targets
OptimalInteractionMatrix(cM, P+, T-, TYPE );
                                    /* flag unacceptable off-diagonal
                                       and return corresponding probe and
                                       target sequences in sets P, T);
InitializeSet (P);                  /* set all elements in set to zero */
InitializeSet (T);
FOR( all probes p+ in P+ )
    FOR( all targets, t- in T-)
    {
        IF( ( p+ NOT cognate to t-) AND ( M(p+ , t-) > € ) )
        {
            FlipOrientation (p+,fp+=p-);         /* flip probe orientation */
            Store (p- in P);
            FlipOrientation (t-[p+], ft-[p+]= t+);   /* flip orientation of
                                                        target cognate to p- */
            Store( t+ in T);
        }
    }
}
```

-continued

```
IF (DESIRED)
    InitiateGroup(P, T);              /* New Group containing
                                         remaining "offending"
                                         probes and targets */
Return( );
```

In accordance with the flow chart in FIG. 3A, this function will be called repeatedly with varying values of the cutoff parameter $\epsilon$ to generate additional steps of strand and group selection. Material Selection—In one embodiment, detection probes are displayed on encoded microparticles ("beads"). The labels associated with encoded beads and the labels associated with the transcripts bound to the probes in the array are preferably fluorescent, and can be distinguished using filters which permit discrimination among different hues. Preferably, sets of encoded beads are arranged in the form of a random planar array of encoded microparticles on a planar substrate permitting examination and analysis by microscopy. Intensity is monitored to indicate the quantity of target bound per bead. This assay format is explained in further detail in U.S. application Ser. No. 10/204,799, filed Aug. 23, 2002, entitled: "Multianalyte molecular analysis using application-specific random particle arrays," hereby incorporated by reference.

The particles to which the probes are attached may be composed of, for example, plastics, ceramics, glass, polystyrene, methylstyrene, acrylic polymers, paramagnetic materials, thoria sol, carbon graphite, titanium dioxide, latex or cross-linked dextrans such as sepharose, cellulose, nylon, cross-linked micelles and Teflon. (See, e.g., "Microsphere Detection Guide" from Bangs Laboratories, Fishers, Ind.). The particles need not be spherical and may be porous. The particle sizes may range from nanometers (e.g., 100 nm) to millimeters (e.g., 1 mm), with particles from about 0.2 micron to about 200 microns being preferred, with particles from about 0.5 to about 5 microns being more preferred. Particles are encoded so as to be correlated with the sequence-specific bead-displayed probes that are placed on the surface of the particles by a chemically or physically distinguishable characteristic, for example fluorescence, uniquely identifying the particle. Chemical, optical, or physical characteristics may be provided, for example, by staining beads with sets of optically distinguishable tags, such as those containing one or more fluorophore or chromophore dyes spectrally distinguishable by excitation wavelength, emission wavelength, excited-state lifetime or emission intensity. The optically distinguishable tags may be used to stain beads in specified ratios, as disclosed, for example, in Fulwyler, U.S. Pat. No. 4,717,655. Staining may also be accomplished by swelling particles in accordance with methods known to those skilled in the art, (See, e.g., Molday, Dreyer, Rembaum & Yen, J. Mol Biol 64, 75-88 (1975); L. Bangs, "Uniform latex Particles, Seragen Diagnostics, 1984). Using these techniques, up to twelve types of beads were encoded by swelling and bulk staining with two colors, each individually in five intensity levels, and mixed in five nominal molar ratios. Alternatively, the methods of combinatorial color encoding described in International Application No. PCT/US 98/10719 (incorporated herein by reference) may be used to endow the bead arrays with optically distinguishable tags.

After encoding, the sequence-specific oligonucleotide probes are coupled to the encoded beads by one of several method, including biotin-mediated noncovalent attachment to streptavidin functionalized encoded beads using oligonucleotide capture probes synthesized to include a 5' biotin and TEG spacer (Synthegen TX) or by direct chemical coupling using, for example, amine-modified capture probes or covalent coupling.

To fabricate a custom array containing a specific probe combination, the encoded, probe-decorated beads are pooled together and assembled into arrays. Many different methods of assembling arrays are possible, including a technique known as LEAPS™ (Light-Controlled Electrokinetic Assembly of Particles Near Surfaces, described in U.S. Pat. No. 6,251,691 which is hereby incorporated by reference). In LEAPS™, the bead arrays are prepared by first providing a planar electrode that is substantially parallel to a second planar electrode (in a "sandwich" configuration), with the two electrodes being separated by a gap, where in the gap is a polarizable liquid medium, such as an electrolyte solution. The surface or the interior of the second planar electrode is patterned to create areas of lowered impedance. The beads are then introduced into the gap. When an AC voltage is applied to the gap, the beads form a random encoded array on the second electrode, in accordance with the patterning, or, in the alternative, in accordance with an illumination pattern on the second electrode. The resulting arrays can exhibit a very high feature density.

In an assay as described herein, the population of particles is encoded with a distinct chemical or physical characteristic that allows the type of particle to be determined before and after the assay. A set of sequence-specific probes, known as a "capture probe set", is used in the assay. The members of a sequence-specific probe set are designed to be complementary to target sequences, specifically cDNA molecules. Each member of a capture probe set is designed—using methods described herein—to have a unique complementary region with one "cognate" cDNA target molecule. To facilitate detection of captured targets, cDNA molecules are fluorescently labeled by incorporation, during reverse transcription, of labeled dNTPs at a preset molar ratio, the total amount of incorporated dNTP varying with the length of the (reverse) transcript. Instead of, or in addition to, hybridization-mediated capture, the assays herein also include elongation-mediated detection; cDNA molecules are added in the presence of a solution containing dNTPs, or ddNTPS, and DNA polymerase to elongate the cDNA on those probes whose 3' end is complementary to the captured target. The dNTP/ddNTP mixture contains at least on labeled dNTP or ddNTP, in order to incorporate fluorescent label in the elongated probe.

Either prior to, or subsequent to recording of the decoding image, the array of encoded particles is exposed to the cDNA target molecules under conditions permitting capture to particle-displayed probes. After a reaction time, the array of encoded particles is washed 3 times with 10 µl of 1×TMAC to remove remaining free and weakly annealed cDNA target molecules. An assay image of the array is then taken to record the optical signal of the probe-cDNA complexes of the array. Because each type of particle is uniquely associated with a sequence-specific probe, the decoding step, completed prior to performing the assay, permits the identification of annealed cDNA molecules whose respective abundances—relating directly to the abundances of the corresponding original mRNA messages—are determined from the fluorescence intensities of each type of particle.

A fluorescence microscope is used to decode particles in the array and to detect assay signals from the array of probe-captured cDNA molecules. The fluorescence filter sets in the decoder are designed to distinguish fluorescence produced by encoding dyes used to stain particles, whereas other filter sets are designed to distinguish assay signals produced by the dyes associated with the transcripts/amplicons. A CCD camera may be incorporated into the system for recording of decoding and assay images. The assay image is analyzed to determine the identity of each of the captured targets by correlating the spatial distribution of signals in the assay image with the spatial distribution of the corresponding encoded particles in the array.

Concurrent Optimization of Probe Selection—Concurrent optimization herein refers to an iterative process of making a selection of conversion probes ("primers"), followed by a selection of detection probes ("capture probes"). These two steps of selection are interdependent ("coupled"). For example, in the case of multiplexed expression monitoring, the selection of conversion probes, preferably placed so as to produce short converted sequences, reduces the sequence space available for the placement of detection probes, and the selection of minimally cross-reacting detection probes in turn may require an increase in the available sequence space and hence call for the modification of the first selection. While the methods herein are described below with reference to reverse transcription (RT) and subsequent hybridization-mediated detection and quantitative determination of cDNA sequences, these methods can also be applied to other genetic-related assays (including genotyping assays), and to related problems of probe selection.

Interaction Matrices—Concurrent optimization is attained by iterative approximate diagonalization of a first interaction matrix $\Gamma=(\gamma_{jk})_{j=1,M; k=1, N\leq M}$ composed of elements governing the interaction between conversion probes, $\pi_j$, and original targets, $T_k$, e.g., mRNAs, and diagonalization of a second interaction matrix, $C=(c_{ij})_{i=1,P; j=1, M\leq P}$, composed of elements governing the interaction between detection probes, $p_i$, and converted targets, e.g., cDNAs, $t_j$, the j-th cDNA sequence representing the reverse transcript incorporating the j-th RT primer.

End-weighted Hamming Distance Function—The elements, $\gamma_{jk}=\gamma_{jk}$ (s), of the interaction matrix $\exists$ represent a sequence similarity score which is computed for all possible alignments of the j-th RT primer and k-th mRNA target in terms of an end-weighted Hamming distance function, $\chi=\chi(l)$; $1 \in L(\pi_j)$ denotes an index running—in the 3' to 5' direction—over the bases within the j-th primer, $\pi_j$, of length $L(\pi_j)$:

$$\gamma_{jk}(s)=\Sigma_{1 \in L(\pi j)} 1/\chi \quad (1)$$

The function $\chi=\chi(l)$ (see FIG. 1), normalized to a range of [0, 1] and modeled here by $$\chi(l)=\tfrac{1}{2}\{1+\arc tg(\alpha(l-\delta))\},$$

assigns a penalty to each probe-target mismatch in such a way that penalties increase rapidly the closer the location of the mismatch to the primer's 3' terminus. This reflects the fact that proper priming requires a perfect match over a characteristic number of bases near the primer's 3' terminus, while a mismatch located outside this characteristic terminal elongation initiation (TEI) range is tolerated. The parameter $\delta$ permits adjustment of this range by placing the midpoint, $\chi(l=\delta)=\tfrac{1}{2}$ at the position $\delta$ (counting from the primer's 3' terminus); the parameter $\alpha$ permits adjustment of the "steepness", that is, the relative increase in the "penalty" for a mismatch within the TEI range to the normalized score of unity for a mismatch near the primer's 5'end.

A normalized sequence similarity score, $0\leq\gamma^N_{jk}(s)\leq 1$, is readily defined in terms of a maximal mismatch score, $\gamma^{max}_{jk}$, corresponding to a complete mismatch, as follows:

$$\gamma^N_{jk}(s)=1-(\gamma_{jk}/\gamma^{max}_{jk})$$

A perfect match ($\gamma_{jk}=0$) will generate a normalized similarity score of unity, while a complete mismatch will generate a normalized similarity score of 0. Accordingly, the objective of iterative optimization in primer selection corresponds to the approximation of a diagonal unit matrix, $\Gamma^{Opt}=1$, in terms of normalized sequence similarity scores.

In practice, a mismatch limit parameter, $\eta$, is set to limit the number of mismatched base pairs counted in the score to a maximum; for example, for a primer length of L=19, a typical value for $\eta$ might be 5. A threshold score parameter, $\tau$, is set to limit the number of candidate cross-reactivity positions, s, recorded for each primer-target pair, rendering the $\Gamma$-matrix a three-dimensional object in cases involving multiple such candidates. In practice, one may determine to record all candidate subsequences of a given target sequence, $\tau_k$, which produce a normalized similarity score above, say, 0.9; more commonly, the list of candidate subsequences will be sorted and only the most "dangerous" candidate will be recorded in a now two-dimensional $\Gamma$-matrix. In practice, rather than working with $\gamma^N_{jk}$ (s), it is often preferable in the interest of computational efficiency to work with the score $\gamma_{jk}$ (s) and set parameter values accordingly. In this case, optimization will minimize diagonal elements and maximize off-diagonal elements.

Center-weighted Hamming Distance Function—The elements, $c_{ij}=c_{ij}$ (s), of the interaction matrix C represent a sequence similarity score which is computed for all possible alignments of the i-th detection probe, $p_i$, and j-th cDNA target in terms of a center-weighted Hamming distance function, $k=k$ (l); $1 \in L(p_i)$ denotes an index running—in the 3' to 5' direction—over the bases within the i-th probe, $p_i$, of length $L(p_i)$:

$$c_{ij}(s)=\Sigma_{1 \in L(p i)} 1/k \quad (1)$$

The function $k=k$ (l) (see FIG. 2), normalized to a range of [0, 1] and modeled here by a symmetrized version of the function $\chi(l)$, assigns a penalty to each probe-target mismatch in such a way that penalties decrease the farther their location from the probe's central position. This reflects the fact that stable probe-target annealing is most sensitive to a mismatch at or near the center of the probe sequence. As with the $\chi$ function, the parameters $\delta$ permits adjustment of the range of highest penalties while the parameter $\alpha$ permits adjustment of steepness: the larger the $\alpha$-parameter, the more closely the k-function resembles a "square well," as shown in FIGS. 2a and 2b.

A normalized sequence similarity score, $0\leq c^N_{ij}(s)\leq 1$, is readily defined as before in terms of a maximal mismatch score, $c^{max}_{ij}$, as follows:

$$c^N_{ij}(s)=1-(c_{ij}/c^{max}_{ij})$$

A perfect match ($c_{ij}=0$) will generate a normalized similarity score of unity, while a complete mismatch will generate a normalized similarity score of 0. Accordingly, the objective of iterative optimization in probe selection corresponds to the approximation of a diagonal unit matrix, $C^{Opt}=1$, in terms of normalized sequence similarity scores.

As with the end-weighted Hamming distance function, a mismatch limit parameter, E, and a threshold score parameter, T, are set; and the list of candidate cross-reactivity subsequences will be sorted and only the most "dangerous" candidate will be recorded in a two-dimensional C-matrix.

In practice, rather than working with $C^N_{ij}(s)$, it is often preferable in the interest of computational efficiency to work with the score $c_{ij}(s)$ and set parameter values accordingly. In this case, optimization will minimize diagonal elements and maximize off-diagonal elements.

The efficient evaluation of similarity scores as a function of probe-target alignment is analogous to the evaluation of a cross-correlation function and can be implemented in very efficient fashion, for example by way of a matrix multiplication. The methods herein invoke fast string matching functions—available in standard libraries such as the C++ class libraries used in the implementation of these methods to identify base pairing mismatches—and then multiplies each mismatch with a tabulated value of the appropriate weighted Hamming distance function. Source codes relating to the algorithms and specifically to the evaluation of weighted Hamming distance functions by fast string matching are attached as Appendices I and II. These codes are designed for carrying out optimized RT primer and capture probe designs, using end-weighted and center-weighted functions (as explained below) and specific values of the mismatch cut-off parameters.

The resulting similarity score is preferable to the Hamming distance commonly used in the construction of DNA codes in which free energy considerations are ignored, and also is preferable to the NN models for the evaluation of the free energy of probe-target complex formation which does not provide an appropriate representation of priming while requiring detailed inspection to identify each base, thereby unnecessarily reducing the efficiency of evaluating cross-correlations.

Concurrent Optimization of Interaction Matrices—The formulation of the optimization problem herein resembles the classic problem of matrix or operator diagonalization which is solved by determination of eigenvalues—the diagonal matrix elements—and corresponding eigenvectors. In the classic quantum mechanical problem, the concurrent diagonalization of two operators requires that the operators share a common set of orthonormal eigenvectors.

However, probe-target and primer-target interactions may not permit, and in many instances may not require, diagonalization in this strict sense. Thus, in the situations of interest herein, a global definition of the orthonormality criterion in terms of an appropriate similarity score may be possible, but, in practice, an adjustable parameter, namely the similarity score threshold, serves as the measure of orthonormality which may differ for different probe-target pairs. In addition, the selection of conversion probes generally is performed in a larger sequence space than is the selection of detection probes, and it may not be desirable to make that selection under the condition of being restricted to a common (complementary) set of probes for both steps. Thus, only in the special case of selecting detection probes by forming the reverse complement of a selected set of RT primers are conversion and detection probes directly related. This choice usually is undesirable because capture probes will form a complex with free primers remaining in the reaction. Preferably, detection probes for cDNA sequences will be directed to a subsequence located in proximity to the cDNA's 5' terminus while RT primers represent the cDNA's 3' terminus. In this case, the selection of primers restricts the selection of capture probes but does not predetermine it.

In view of these considerations, disclosed is a method of iteratively improving the selection of primers and probes in a manner which corresponds to the concurrent iterative approximation of diagonal interaction matrices. This iterative method involves the fast evaluation of the sequence similarity scores for all possible alignments of each probe in the set with all subsequences on all target sequences to be included in the same reaction. The initial selection of RT conversion probes and detection probes generally will be based on a set of empirical design rules. Iterations are performed with the objective of minimizing a suitable measure of deviation of off-diagonal elements in the interaction matrices $\Gamma_{Opt}$ and $C_{Opt}$ from zero in accordance with any standard non-linear regression method.

Empirical Design Rules for Initial Selection of RT Primers—Empirical design rules, presented below, guide the initial selection of reverse transcription primers and capture probes for multiplexed gene expression monitoring in order to discriminate between multiple specific mRNAs of interest while attaining high detection sensitivity with minimal non-specific background. These rules provide that whenever possible, RT primers will be selected to enhance the capture efficiency by producing short transcripts, and capture probes will be directed to the transcripts' 5'-ends. Accordingly, the selection of RT primers and that of capture probes for the RT transcripts are closely interrelated.

The empirical design rules involve the following steps in designing RT primer—capture probe sets for multiplexed gene expression profiling:

1—Starting at the 5'end of each target sequence, select a subsequence of ~100 nt;
2—Perform multiple sequence alignment, for example by means of ClustalW (or other programs, e.g., Divide-and-Conquer Multiple Sequence Alignment, as described in Stoye et al., Multiple Sequence Alignment with the Divide-and-Conquer Method, Gene 211, GC45-GC56, 1988) to identify stretches of sequence suitable for the placement of RT primers; these initial sequences preferably display minimal homology with other stretches of sequence in the same or other targets in the set;
3—Place RT primer in the least homologous region within the 100 nt stretch, using BLAST (or equivalent) to minimize the homology between the candidate RT sequence and all other target sequences in order to minimize or exclude non-specific RT priming;
4—Depending on sequence uniqueness, identify a position near each transcript's 5' terminus for placement of the corresponding capture probe; as desirable, a free energy profile may be calculated to identify particularly stable positions of the probe;
5—Check and if necessary refine sequences by means of standard design tools (e.g., Oligo6, Primer3) to exclude hairpins, dimers, GC-rich sequences, etc;
6—Fine tune RT primer—and subsequently capture probes—by analyzing paired alignments of closely related genes (for example, see Example 1, IL-4 and IL-6, Tables I, II):
6.1—Avoid contiguous stretches (n>3), especially GC-rich stretches, of homologous nucleotides
6.2—In case of partial homology, select sequences with contiguous mismatches between homologous bases;
7—Place selected primers and probes into a desirable range of melting temperatures, chosen so as to ensure high stringency in RT as well as hybridization reactions to improve the ratio of specific signal to (non-specific) background.

Note that in practice, sets of RT primers and sets of capture probes are preferably designed so as to accommodate reaction protocols placing the reaction temperature in a range of approximately 3-5 degrees below calculated values of individual RT primer and capture probe melting temperatures.

CoAffinities and Competitive Hybridization—Once an optimal selection of primers and probes has been made, the thermodynamic stability of each probe-target duplex can be evaluated, for example by invoking the standard nearest-neighbor stacking models of the art. There will be one such coaffinity, $K_{ik}$, for each probe-target duplex in accordance with the elements of the interaction matrices. Given these coaffinities, competitive hybridization effects may be explicitly taken into account, as discussed in U.S. application Ser. No. 0/032,657, filed on Dec. 28, 2001, and in Provisional Application No. 60/470,806, filed May 15, 2003.

Algorithm for Concurrent Optimization—A procedure for the systematic iterative concurrent optimization of primer and probe sets can now be summarized as follows in terms of the pseudocode below ("Pseudocode II"). Iterative optimization is readily implemented in accordance with standard non-linear regression methods of the art such as the Marquardt algorithm ("Numerical Recipes in C", Cambridge University Press), and using either an element-specific ("local") or global measure of convergence. The local measure can be based on individual off-diagonal elements of each interaction matrix while a global measure is readily defined, for example, as the sum over all off-diagonal elements in each matrix. In the absence of convergence, it may be advisable to examine the use of antisense probes and to split the original set of target sequences into two and repeat the analysis in accordance with the methods discussed above.

```
                /* see Fig. 1 */
ConstructFunctionLookUpTable (α, δ, L);
Return (FuncPointer);
                /* see Fig. 2 */
ConstructFunctionLookUpTable (α, δ, L );
Return (FuncPointer);
                        /* Apply standard checks and other constraints:
                            Min or max length
                            No hairpins
                            No primer dimers
                            No RT primer/probe dimers
                            Low GC content
                            Preset range of melting temp's
                                Etc;
                                see e.g.: Primer3,
Oligo6*/Check Probe (p);
Return (STATUS = ApplyCriteria (p) );
FOR (all target sequences in set T)
{
    STATUS = FAIL;
    WHILE (STATUS == FAIL)
    {
        p = PlacePrimer ( );    /* Invoke empirical design rules, at
                                   least one primer per mRNA */
        STATUS = CheckProbe (p);
    }
}
Return( );
                        /* Apply one or more of shift,
                            pad_or_prune, etc operations
                            to modify primer and probe
                            sequences */
ModifyProbeSet (P, DevMatrix, TYPE)
FOR (all probes in set P flagged in DevMatrix)
{
    IF (TYPE == E)
    {
        IF (DESIRABLE)    /* Remain as close as possible to
                             5' end - as defined by MAX_SHIFT*/
            ShiftSeq( AWAY FROM 5' END OF TARGET (mRNA) );
            Pad_or_Prune_3'End ( );
    }
    ELSE IF(TYPE == C)
    {
        ShiftSeq ( IN EITHER DIRECTION );
```

```
        Pad_5'_and 3'Ends ( );
    }
}
Return( );
}
ComputeInteractionMatrix(M, P, T, TYPE)
/* Boolean TYPE = E, C */
FOR (all probes in set P)
{
    p = SelectProbe (P);
    FOR (all targets in set T)
    {
        t= SelectTarget (T);
                                /* Compute cross-
                                   correlation, full
                                   sequence overlap only
                                   */
        s = 0; WHILE (s ≠ L(T) – L(P))
        {
            IF(TYPE == E)    Func = χ ( ); / * Set func pointers */
            IF(TYPE == C)    Func = k ( );
                                /* Identify cross-
                                   reactivity candidate
                                   seq's in target t on
                                   basis of cross-
                                   matching score using χ
                                   or k function */
            CandSeq = ComputeScore (p, t, Func);
                                /* Unless RANK option
                                   is turned off, place
                                   "most dangerous"
                                   candidate seq into
                                   interaction matrix at
                                   element p, t;
                                   otherwise, 3d matrix /
            IF (RANK == ON)
                M(p, t) = SortCandidateScores( CandSeq);
            s += 1;
        }
    }
}
Return( );
OptimalInteractionMatrix( M, P–, T+, TYPE )
                                /* Set Up Iteration */
TargetSeq (τ_1, τ_2, ... , τ_N);    /* Read in and store given target
                                       sequences */
π = SelectPrimer Set (T);       /* Apply empirical rules to construct
                                   initial primer set */
χ = Evaluate_χ(α, δ, L_{CP});     /* Evaluate end-weighted Hamming
                                   distance function for conversion
                                   probes of length L_{CP}
                                   Return pointer to tabulated
                                   function χ(l) */
k = Evaluate_k (a, d, L_{DP} );   /* Evaluate center-weighted Hamming
                                   distancefunction for detection probes
                                   of length L_{DP} ;
                                   Return pointer to tabulate function k (l) */
LOOP:
Perform Iterative Optimization of Conversion Probe – Capture Probe Sets
by Minimizing Off-diagonal Elements in Γ and C Interaction Matrices
r = 0; DO
{
    r += 1;
                                /* Construct Γ Matrix using
                                   end-weighted Hamming
                                   distance function */
    ComputeInteractionMatrix( Γ, π, T, TYPE = E);
                                /* Record all off-diag matrix
                                   elements exceeding preset
                                   threshold */
    DevΓ = EvaluateDeviation (Γ );
/* Construct C Matrix using center-weighted Hamming distance
function */
    ComputeInteractionMatrix( C, P, T, TYPE = C);
    DevC = EvaluateDeviation (C);
    IF( r > 0 )
    {
        ModifyProbeSet (π, DevΓ, E);
        ModifyProbeSet (P, DevC, C);
    }
```

-continued

```
} WHILE ( ( (MaxDevΓ > ε_Γ ) OR (MaxDevC > ε_C)) )OR
(K == K_MAX) );
```

The examples below provide further details regarding the making and using of the invention.

Example I

Generic Procedure

An illustrative procedure for expression profiling using Random Encoded Array Detection (READ) is as follows. First, total RNA is isolated from blood samples using Qiagen silica-gel-membrane technology. DNA oligonucleotide primers for reverse transcription (RT) are added to the extracted RNA samples, the primer sequences preferably selected to target a subsequence near the 3' regions of the mRNAs of interest. To facilitate mRNA denaturation and primer hybridization, the samples are heated to 65° C. and then are gradually cooled to room temperature. Next, reverse transcription is initiated by adding reverse transcriptase and dNTPs, a certain fraction of which are fluorescently labeled to produce labeled cDNAs. Following completion of reverse transcription, the mRNA templates are digested using RNase. For multiplexed analysis, the mixture of fluorescently-labeled cDNAs is then placed in contact with an array of encoded microparticles ("beads") under conditions permitting hybridization-mediated capture of targets to bead-displayed capture probes; for example, typical conditions include incubation for 30 minutes, at 50° C. in 1×TMAC buffer. Random encoded arrays of encoded microparticles ("beads") are assembled on silicon chips as described herein. Encoded beads display sequence-specific oligonucleotide capture probes preferably directed to subsequences near the 5' end of the cDNAs in the mixture.

Example II

Effects of Transcript Length and Probe Placement on Capture Efficiency

The reduction in transcript length and the selection of capture probes directed to cDNA subsequences located near the 5' end of long transcripts enhance the apparent affinity governing capture efficiency and hence assay signal and sensitivity. For example, it has been found experimentally that for a transcript of length 500 nt, the use of capture probes directed to a transcript subsequence near the 5'-end ("terminal probes") produces an enhancement of ~1.5 in assay signal over that recorded with capture probes directed to the interior ("internal probes"). Both enhancements reflect the importance of entropic effects which, particularly in the concentrated regime, diminish the sequence-dependent affinity, K, to an effective affinity, $K_{eff}(L)<K$. This has significant implications for the design of capture probes as well as transcripts. Experimental support is set forth in a provisional application to be filed shortly.

In the dilute regime, entropic effects arise from the requirement that the incoming target assume one of a small number of configurations permitting the formation of a complex with immobilized probes. This implies a free energy penalty arising from the reduction in the target's configurational entropy. This single molecule effect is apparent from the results above: placement of the capture subsequence near the transcript's 5'-end facilitates formation of a probe-target complex without major reconfiguration of the target, an effect that will be increasingly pronounced the longer the target. In the concentrated regime, entropic effects arise from the "crowding" of captured targets which preferentially assume configurations that minimize interpenetration. Crowding also leaves increasingly limited space to accommodate additional incoming targets, which now must assume configurations compatible not only with capture and complex formation but with the available spatial arrangement defined by the population of previously captured targets.

Example III

Multiplexed Cytokine Expression Monitoring

Empirical Primer and Probe Selection

The empirical design rules disclosed herein were applied to the analysis of the nine cytokine (and control) targets of interest. Six sets of RT primers were designed to generate cDNAs varying from ~50 nt to ~70 nt in length, and six "5'-end-directed" capture probes were designed to detect the cDNAs. Based on predicted melting temperatures (Table I) for the selected RT primers and capture probes, an optimal RT reaction temperature in the range of 42° C.-50° C. and an optimal hybridization temperature in the range of 55° C.-58° C. is anticipated.

Preparation of 9 Human Cytokine In-Vitro Transcripts—To demonstrate multiplexed expression monitoring using custom BeadChips for the quantitative multiplexed detection of a designated set of clinically relevant genes, for example to assess, rapidly and reliably, exposure to pathogens and threat agents, we have generated a reference panel of nine (9) human cytokine mRNA targets including two (2) endogenous (internal) controls and two (2) negative controls (Table 1).

The full-length cDNA clones of the selected cytokines were characterized by sequencing and recovered from a filter in a form of plasmid DNAs containing specific cytokine cDNA inserts in a pCMV6 vector (OriGene Technologies, Inc.). Specifically, each cDNA clone was transformed into a competent bacterial host, and transformed cells were plated on LB/ampicillin plate and grown in culture the single colony. DNA plasmid purification was performed using a mini prep kit (Qiagen).

Using this protocol, cDNA plasmid preparations for seven cytokines (IL-2, -4, -6, -8, -10, TNF-α and IFN-γ) and two endogenous controls (GAPDH, Ubiquitin) were produced and characterized by sequencing (Origene Technologies).

The PCR primers to the cloning vector sequence were designed to permit amplification of all cDNA inserts with a standard primer pair, thus eliminating the substantial cost of target-specific PCR amplification. Specifically, positioning of the forward PCR primer upstream of the T7 promoter sequence—located next to the cloning EcoRI site of every cytokine insert (cDNA)—enables T7 in-vitro transcription of only the specific cDNA sequence located at the 5'-end of the Trizol extraction and isopropanol precipitation, which were checked for purity by denaturing polyacrylamide gel electrophoresis. Using this protocol, cDNA clones were amplified using a pair of vector-specific primers and in-vitro transcription was performed (MegaScript, Ambion) using the T7 promoter of the vector sequence to produce nine RNA transcripts. Following RNA purification, approximate concentrations were determined by optical absorption spectroscopy, followed by dilution of each RNA template to 32.5 fmoles per reaction.

Using selection rules for RT primer and capture probe selection as set forth herein, 11 sets of capture probes with the corresponding reverse transcription primers specific for each mRNA of interest (Table I) were designed. Based on calculated melting temperatures for the selected RT primers and capture probes, the RT reaction was performed using a 3-step profile, starting with RNA denaturation at 65° C. for 5 min, followed by primer annealing and extension at 50° C. for 30 min, then at 40° C. for 20 min. On chip hybridization was performed at 55° C., which was an average Tm of nine probes.

TABLE 1

Set of 9 human Cytokine cDNA Clones for Multiplexed Analysis: Designs of Reverse Transcription Primers and Capture Probes of the Analytes.

| Accession No. Number | Sample Description | RT Primer | Capture Probe | | Probe Bead Code |
|---|---|---|---|---|---|
| | Undergraduate | | | | |
| 1 NM_000206 | Homo sapiens interleukin 2 receptor, gamma (II2RG), mRNA | ATTGGGCGTCAGAATTGTCG 20-MER, 62.0C SEQ ID NO. 1 | ATGTTGAAGCCATCATTAC-CATTC 24-MER, 62.6C SEQ ID NO. 2 | | G5B |
| 2 NM_152899 | Homo sapiens interleukin 4 induced 1(II4I1), transcript variant 1, mRNA | GGACGAGGACGAGGAGGT Tm = 63.6C SEQ ID NO. 3 | TGTCCTGCTGTCACCAAGAG 20-mer, Tm = 63.7C SEQ ID NO. 4 | 18-mer, | G5C |
| 3 NM_000565 | Homo sapiens interleukin 6 receptor (IL6R), mRNA | GCTAATGGGAACCGGGC 17-Mer, Tm-61.5C SEQ NO. 5 | CAGTGTGTGTAGAGAGCCGG 20-Mer, Tm = 63.TC SEQ ID NO. 6 | | G5D |
| 4 NM_000584 | Homo Sapiens interleukin 8 (IL8), mRNA | TCTTTAGCACTCCTTGGCAAA 60.8C SEQ ID NO. 7 | GTGTAGGCACTGAGGACGG 19-mer, 64.3 SEQ ID NO. 8 | 21-mer, | G5E |
| 5 NM_001558 | Homo sapiens interleukin 10 receptor, alpha (IL10RA), mRNA | ATGAGCGTCTGAGCCAAGA 19-mer, Tm = 62.0C SEQ ID NO. 9 | ATGCTGCCGTGCCTCGTAG 19-mer, Tm = 66.1C SEQ ID NO. 10 | | G5F |
| 6 NM_001066 | Homo sapiens tumor necrosis factor receptor superfamily, member 1B (TNFRSF1B) | TCATAGTATTCTCTGAGCCGG 59.4C SEQ ID NO. 11 | CAGGTGGCATTTACACCCTACG 22-mer, 64.3C SEQ ID NO. 12 | 21-mer, | G3B |
| 7 NM_018955 Internal control | Homo sapiens ubiquitin B (UBB), mRNA | GTCTTGCCGGTAAGGGTT Tm = 60.4C SEQ ID No. 13 | GCAGGATCCTGGTATCCGCTA 22-mer, 64.3C SEQ ID NO. 14 | 18-mer, | G3C |
| 8 NM_002046 | Homo sapiens glyceraldehydes-3-phosphate dehydrogenase (GAPD), mRNA | ACGGTGCCATGGAATTTGC Tm = 62.8 C SEQ ID NO. 15 | GGAGTCAACGGATTTGGTCGT 21-Mer, Tm = 63.6c SEQ ID NO. 16 | 19-Mer, | G3D |
| 9 NM_000416 | Homo Sapiens Interferon gamma receptor 1 (IFNGR1)mRNA | GTGTAGGCACTGAGGACGG 19mer Tm = 63C (SEQ ID NO: 17) | -GCATGGCTCTCCTCTTCTCC 21-mer, Tm = 635c SEQ ID NO. 18 | | G3E G2A |
| 10 Neg control | Control for unspecific binding of nucleic aciD | -NONE | -Oligo-C18 (SEQ ID NO: 117) | | |
| 11 Neg Control | Kanamycin mRNA not present in a multiplexed mxs | NONE | TACAAGCTTGGGCGTGTCTCTC | | G2B |

TABLE II

Initial choice of RT Primers (highlighted by underlined italics) and capture probes (highlighted by underlining) based on empirical design rules using multiple sequence alignment but not optimization; homologous bases are indicated as *

1A. Alignment of 5'-end seques of IL-4 and IL-6 clones

```
(SEQ ID NO. 20)
NM_152899CCGCGCTGTCCTGCTG--TCACCAAGAGC-TGGAGACACCATCTCCCACCGAGAGTCAT          56
(SEQ ID NO. 21)
NM_000565CGCGGGGCCGAGGGACTCGCAGTGTGTGTAGAGAGCCGGGCTCCTGCGGATGGGGGC            60
* * *  * * **  * * * **** *  ****  * ** *
(SEQ ID NO. 22)
NM_152899, IL-4GGCCCCATTGGCCCTGCACCTCCTCGTCCTCGTCCCCATCCTCCTCAG              104
(SEQ ID NO. 23)
NM_000565, IL-6TGCCCC-CGGGGCCTGAGCCCGCCTGCCCGC-CCACCGCCCCGCCC-                104
******* ****  ** **  * ** **  * *
```

1B. Alignment of 5'-end sequences of IL-6 and IL-10 clones

```
(SEQ ID NO. 24)
NM_000565, IL- 6CGGCGCGGGGCCGAGGGACTCGCAGTGTGTGTAGA-GAGCCGG-GCTCCTGCGGATGGGG   58
SEQ ID NO NO. 25)
NM_001558, IL-10 CGCGCAGGCC----GGCTCCGCTCCGGCCCCGGACGATGCGGCGCGCCCA-GGATGCTG     54
(SEQ ID NO. 26)
NM_000565, IL-6GC-TGCCCCCGGGGCCTGA-GCCCGC-CTGCCCGCCCACCGCCCCGCCC-             104
(SEQ ID NO. 27)
NM_001558, IL-10 CCGTGCCTCGTAGTGCTGCTGGCGGCGCTCCTCAGCCTCCGTCTTGGCTC              104
* **** *  * *** * * ** ** * * **  *** * * *
```

2A. Alignment of 5'-end sequences of GAPDH and INF-gamma clones

```
(SEQ ID NO. 28)
NM_002046, GAPD--TTCGACAGTCAGCCGCATC----TCTTTTTGCGTCGCCAGCCGAGCCACATCGCTNAG   54
(SEQ ID NO. 29)
NM_000416, INFCCAGCGACCGTCGGTAGCAGCATGGCTCTCCTCTTTCTCCTACC---CCTTGTCATGCAG    57
**** *** *  *** *    *** *   ** **  **   **    **  **
(SEQ ID NO. 30)
NM_002046ACACCATGGGGAAGGTGAAGGTCGGAGTCAACGGATTTGG-TCGTATTGGGCG            106
(SEQ ID NO. 31)
NM_000416GG--TGTGAGCAGGGCTGAGATGGGCACCG-CGGATCTGGGGCCGTCCTCAG--           106
** * * **   ** * **   *  ***** ***   *** *  *
```

2B. Alignment of 5'-end sequences of GAPDH and Ubiquitin clones

```
(SEQ ID NO. 32)
NM_018955, UBBTGGACGTGGTTGGTGATTGGCAGGATCCTGGTATCCGCTAACAG----GTCAAAATGCAG   56
(SEQ ID NO. 33)
NM_002046, GAPD--------TCGACAGTCAGCCGCATCTTCTTTTGCGTCGCCAGCCGAGCCACATCGCTN     52
* *   * ** *** * * **  *** * ** * **
(SEQ ID NO. 34)
NM_018955AT-CTTCGTGAAAACCCTTACCGGCAAGACCATCACCCTTGAG---GTGGAGC-           105
(SEQ ID NO. 35)
NM_002046AGACACCATGGGGAAGGTGAAGGTCGGAGTCAACGGATTTGGTCGTATTGGGCG            106
* * * ** * * **** * * ***      * * **
```

3. CLUSTAL W (1.82) multiple sequence alignment of 6 human cytokines:

```
(SEQ ID NO. 36)
NM_152899CCGCGCTGTCCTGCTG---TCACCAAGAGC-TGGA-GACACCA-TCTCCCACCGAGAGTC     54
(SEQ ID NO. 37)
NM_000565CGCGCGGGGCCGAGGGACTCGCAGTGTGTGTAGA-GAGCCGG-GCTCCTGCGGATGGGG    58
(SEQ ID NO. 38)
NM_001558-CGCGCAGGCCGGCT-----CCGCTCCGGCCCCGGACGATGCGGCGCGCCCA-GGATGCTG   54
(SEQ ID NO. 39)
NM_018955-TGGACGTGGTTGGTGA--TTGGCAGGATCCTGGT--ATCCG-----CTAACAGGTCAAA    50
(SEQ ID NO. 40)
NM_000416-CCAGCGA--CCG------TCGGTAGCAGCATGGCTCTCCTCTTTCTCCTACCCCTTGTC    51
(SEQ ID NO. 41)
NM_002046-TTCGACAGTCAGCCGCA-TCTTCTTTTGCGTCGC-CAGCCGA--GCCACATCGCTNAG-   54
***
(SEQ ID No. 42)
NM_152899ATG-GCCCCATTGGCC---CTGCAC------CTCCTCGTCCTCGTCCCCATCCTC-CTCA   103
(SEQ ID NO. 43)
NM_000565GCT-GCCCC-CGGGGC---CTGAGC------CCGCCTGCCCGC-CCACCGCCCCG-CCC-   104
(SEQ ID NO. 44)
NM_001558CCGTGCCTCGTAGTGCTG-CTGGCG------CGCTCCTCAGC--CTCCGTCTTGGCTC-    104
(SEQ ID NO. 45)
NM_018955ATGCAGATCTTCCG-------TGAAA------ACCCTTACCGGCAAGACCATCACCCTTGA    97
(SEQ ID NO. 46)
```

TABLE II-continued

Initial choice of RT Primers (highlighted by underlined italics) and capture probes (highlighted by underlining) based on empirical design rules using multiple sequence alignment but not optimization; homologous bases are indicated as *

| | |
|---|---|
| NM_000416ATGCA_GGGTGTGAGCAG_GGCTGAGATGGGCACCGCGGATCTGG--GGCCGTC----CTCA (SEQ ID NO: 47) | 105 |
| NM_002046----_ACACCATGGGG_AAG-GTGAAG------GTCGGAGTCAACGGATTTGGTCGTATTGG | 103 |

MultiplexedExpression Monitoring: In-vitro Transcripts multiplexed RT reaction was performed using a set of nine gene-specific RT primers to produce a pool of nine Cy3-labeled cDNAs in accordance with an optimized protocol described in co-pending Provisional Application No. 60/544,533 (relating to expression profiling), but using a 3-step temperature profile as discussed above. The empirical design rules were used to select RT primers so as to produce cDNAs 50 nt to 70 nt in length while minimizing cross-hybridization see above). This pool of cDNAs was placed, without any purification, onto a chip surface (a "BeadChip") containing eleven types of encoded beads displaying specific capture probes designed for the set of seven cytokine cDNAs (note that in the multiplexed assay, IL-6 was omitted from the RT reaction to provide an indication of the low level of non-specific hybridization) as well as two endogenous positive controls and two negative controls, namely a oligo-C18 (SEQ ID NO: 117) and Kanamycin. The BeadChips included about 300 beads for each of the cDNAs, and this redundancy provides an added level of reliability. More specifically, interaction matrices (see FIGS. 4A and 4B) representing two sets of control experiments from signals generated with empirical design rules for primers/probes were generated. The first interaction matrix (FIG. 4A, upper matrix) is generated from 9 separate BeadChips using only one target and one corresponding gene-specific RT primer in each RT reaction, following which the resulting cDNA is reacted, under hybridizing conditions, to a chip with eleven immobilized capture probes (FIG. 4A, upper matrix). The matrix shows the fluorescent signal generated from the 9 cDNA targets contacting the eleven capture probes. The diagonal (highlighted) of the matrix corresponds to the interaction between perfectly matched probe and target sequences. These fluorescent signals should be at least two-fold higher than nonspecific background generated from no target and negative controls in order to score the fluorescent signal as a positive one. If any data point in the off diagonal matrix shows a positive signal it is considered to be a result of cross-reaction between the capture probe and hybridized cDNA, as shown in FIG. 4A, upper panel, probe 5. The second control data set (FIG. 4A, lower matrix) is generated from 9 BeadChips when all 9 mRNA targets but only one specific RT primer were added into the RT reaction at a time. The data analysis was performed as above, where the diagonal data represents a perfect match between RT primers and mRNA sequences. The off-diagonal positive signals represent cross-reactions between RT primers and mRNA targets. The results obtained using primers and probes selected in accordance with the empirical design rules, demonstrate the ability of the Random Encoded Array Detection (READ) format of multiplexed analysis to simultaneously determine expression levels of multiple designated cytokine genes. However, two mRNA targets in a 9-plex assay, namely, TNF-α and GAPDH, exhibited signal intensity close to the marginal threshold of the background signal; probably as a result of cross-reactive binding of the corresponding RT primers to the non-designated mRNA targets in the multiplexed sample pool. (Note that the signal to noise for each was 1.5 (FIG. 4A, last line, FIG. 4B)). These results indicated the need for optimization of primer/probe design rules, in particular, using the computational tools based on the mathematical algorithms set forth above.

Example IV

Multiplexed Cytokine Expression Monitoring

Optimized Primer and Probe Selection

To improve the performance of the multiplexed expression monitoring design of Example III, the "empirically selected" reverse transcription primers and capture probes of Example III—designed for the reference panel including nine (9) clinically relevant human cytokine mRNA targets and two (2) endogenous (internal) controls and two (2) negative controls (Table I)—were optimized using the methods of the invention, taking into account the critical role of entropic effects discussed in Example II above. A considerable improvement in the specificity of the multiplexed ("9-plex") assay was achieved, as shown by comparing the results in FIGS. 4A and 4B (before optimization) with those in FIGS. 4C and 4D (results following optimization).

Using the optimized design rules for RT primer and capture probe selection, 11 sets of capture probes with the corresponding reverse transcription primers specific for each cytokine mRNA in Tables 4A and 4B were re-designed, as shown in Table III. To increase specificity of hybridization reactions between RT primers and targets, the length of primer sequences was extended to ~20 nucleotides in length. Based on calculated melting temperatures for the re-designed RT primers and capture probes, the RT reaction was performed with a higher stringency than in Example III, using a 2-step profile, starting with RNA denaturation at 70° C. for 5 min, followed by primer annealing and extension at 52° C. for 60 min. On chip hybridization was performed at 57° C.—an average Tm of the nine re-designed probes.

Next, a multiplexed RT reaction was performed on nine in vitro transcribed RNAs, containing 32 femtomoles of each message, using a set of nine gene-specific RT primers to produce a pool of nine Cy3-labeled cDNAs optimized in accordance with the 2-step temperature incubation protocol as discussed above. Specifically, optimized design rules were used to select RT primers so as to produce cDNAs from 60 nt to 200 nt in length while minimizing cross-hybridization.

This pool of directly labeled Cy3-cDNAs, containing 16 femtomoles of each added mRNA, was placed, without any purification, onto a BeadChip containing eleven types of encoded beads displaying specific capture probes designed for the set of seven cytokine cDNAs as well as two endogenous positive controls and two negative controls, namely a oligo-C18 (SEQ ID NO: 117) and Kanamycin. The results presented in FIG. 4C (last two lines) and 4D demonstrate multiplexed reproducible detection of six cytokine cDNAs—

IL-6 having been omitted from the RT reaction to provide an indication of the low level of non-specific hybridization. The signal to noise ratios were reproducible within the range from 3.5 to 6 (see table in FIG. 3, Plot 2), that confirms statistical significance of signal output for every message detected. The data analysis using the interaction matrix performed as described earlier, confirmed reliable selection of unique primer/probe sequences and validity of fluorescent signal for the v.2 designs generated with a computational tool (See diagonal and off diagonal data point in FIG. 2, matrix vs.2). Bead Chips included ~300 beads for each of the cDNAs—this redundancy provides an added level of reliability.

Optimization of Reverse Transcription and Hybridization Conditions on BeadChip for Multiplexed Analysis of Human Cytokine RNAs—Eleven sets of capture probes with the corresponding reverse transcription primers specific for each mRNA of interest were re-designed using the design optimization rules for RT primer and capture probes (Table III). To increase specificity of hybridization reactions between RT primers and targets, the length of the primer sequences was extended to ~20 nucleotides. Based on calculated melting temperatures for the re-designed RT primers and capture probes, the RT reaction was performed with a higher stringency than earlier, using a 2-step profile, starting with RNA denaturation at 70° C. for 5 min, followed by primer annealing and extension at 52° C. for 60 min. On chip hybridization was performed at 57° C.—an average Tm of the nine re-designed probes. Next, a multiplexed RT reaction was performed on 9 in vitro transcribed RNAs, containing 32 femtomoles of each message, using a set of nine gene-specific RT primers to produce a pool of nine Cy3-labeled cDNAs in accordance with the 2-step temperature incubation protocol, optimized as discussed above. Specifically, computational design rules set forth in detail in a co-pending provisional application (No. 60/544,533) were used to select RT primers so as to produce cDNAs from 60 nt to 200 nt in length while minimizing cross-hybridization (see above).

The results presented in FIGS. 4C (last two lines) and 4D demonstrate multiplexed reproducible detection of eight cytokine cDNAs, IL-6 having been omitted from the RT reaction to provide an indication of the low level of non-specific hybridization. The signal to noise ratios were reproducible within the range from 3.5 to 6 (see FIGS. 4C and 4D), confirming the statistical significance of signal output for every message detected in the 9-plex assay.

TABLE III

Set of 7 Human Cytokine cDNA Clones, 2 endogenous controls and 2 negative controls for Multiplexed Analysis on BeadChip: VERSION 2.0 Designs of Reverse Transcription Primers and Capture Probes.

| No. | Accession Number | Sample Description | RT primer | Capture Probe | Bead Code |
|---|---|---|---|---|---|
| 1 | NM_000206 | Homo sapiens interleukin 2 receptor, gamma (IL2RG), mRNA | ATTGGGCGTCAGAATTGTCG 20-mer, 62.0C SEQ ID NO. 48 | ATGTTGAAGCCATCATTACCATTC 24-mer, 62.6C SEQ ID NO. 49 | G5B |
| 2 | NM_152899 | Homo sapiens interleukin 4 induced 1 (IL4I1), transcript variant 1, mRNA | GGACGAGGACGAGGAGGT 18-mer, Tm = 63.6C SEQ ID NO. 50 | TGTCCTGCTGTCACCAAGAG 20-mer, Tm = 62.7C SEQ ID NO. 51 | G5C |
| 3 | NM_000565 | Homo sapiens interleukin 6 receptor (IL6R), mRNA | GCTAATGGGAACCGGGC 17-mer, Tm = 61.5C SEQ ID NO. 52 | CAGTGTGTGTAGAGAGCCGG 20-mer, Tm = 63.1C SEQ ID NO. 53 | G5D |
| 4 | NM_000584 | Homo sapiens interleukin 8 (IL8), mRNA | TCTTTAGCACTCCTTGGCAAA 21-mer, 60.8C SEQ ID NO. 54 | GTGTAGGCACTGAGGACGG 22-mer, 64.3 SEQ ID NO. 55 | G5E |
| 5 | NM_001558 | Homo sapiens interleukin 10 receptor, alpha (IL10RA), mRNA | ATGAGCGTCTGAGCCAAGA 19-mer, Tm = 62.0C SEQ ID NO. 56 | ATGCTGCCGTGCCTCGTAG 22-mer, Tm = 66.1C SEQ ID NO. 57 | G5F |
| 6 | NM_001066 | Homo sapiens tumor necrosis factor receptor superfamily, | TCATAGTATTCTCTGAGCCGG 11-mer, 59.4C SEQ ID NO. 58 | CAGGTGGCATTTACACCCTACG 22-mer, 64.3C SEQ ID NO. 59 | G3B |
| 7 | NM_018955, Internal control | Homo sapiens ubiquitin B (UBB), mRNA | GTCCTTGCCGGTAAGGGTT 18-mer, Tm = 60.4C SEQ ID NO. 60 | GCAGGATCCTGGTATCCGCTA 21-mer, Tm = 64.4.C SEQ ID NO. 61 | G3C |
| 8 | NM_002046, Internal control | Homo sapiens glyceraldehyde-3-phosphate dehydrogenase (GAPD), mRNA | ACGGTGCCATGGAATTTGC 19-mer, Tm = 62.8 C SEQ ID NO. 62 | GGAGTCAACGGATTTGGTCGT 21-mer, Tm = 63.6C SEQ ID NO. 63 | G3D |

TABLE III-continued

Set of 7 Human Cytokine cDNA Clones, 2 endogenous controls and 2 negative controls for Multiplexed Analysis on BeadChip: VERSION 2.0 Designs of Reverse Transcription Primers and Capture Probes.

| Accession No. Number | Sample Description | RT primer | Capture Probe | Bead Code |
|---|---|---|---|---|
| | Undergraduate | | | |
| 9 NM_000416 | Homo sapiens interferon gamma receptor 1 (IFNGR1), mRNA | GTGTAGGCACTGAGGACGG (SEQ ID NO: 64) | GCATGGCTCTCCTCTTTCTCC (SEQ ID NO: 65) | G3E |
| 10 Neg control | Control for unspecific binding of nucleic acids | none | Oligo-C18 (SEQ ID NO: 117) | G2A |
| 11 Neg control Non-human | Kanamycin mRNA Not present in a multiplexed mix | None | TACAAGCTTGGGCGTGTCTC 20-mer, Tm = 63.4C SEQ ID NO. 66 | G2B |

Example V

Detection of Nucleic Acid Subsequences Using Transcription Amplification

Figure 9:
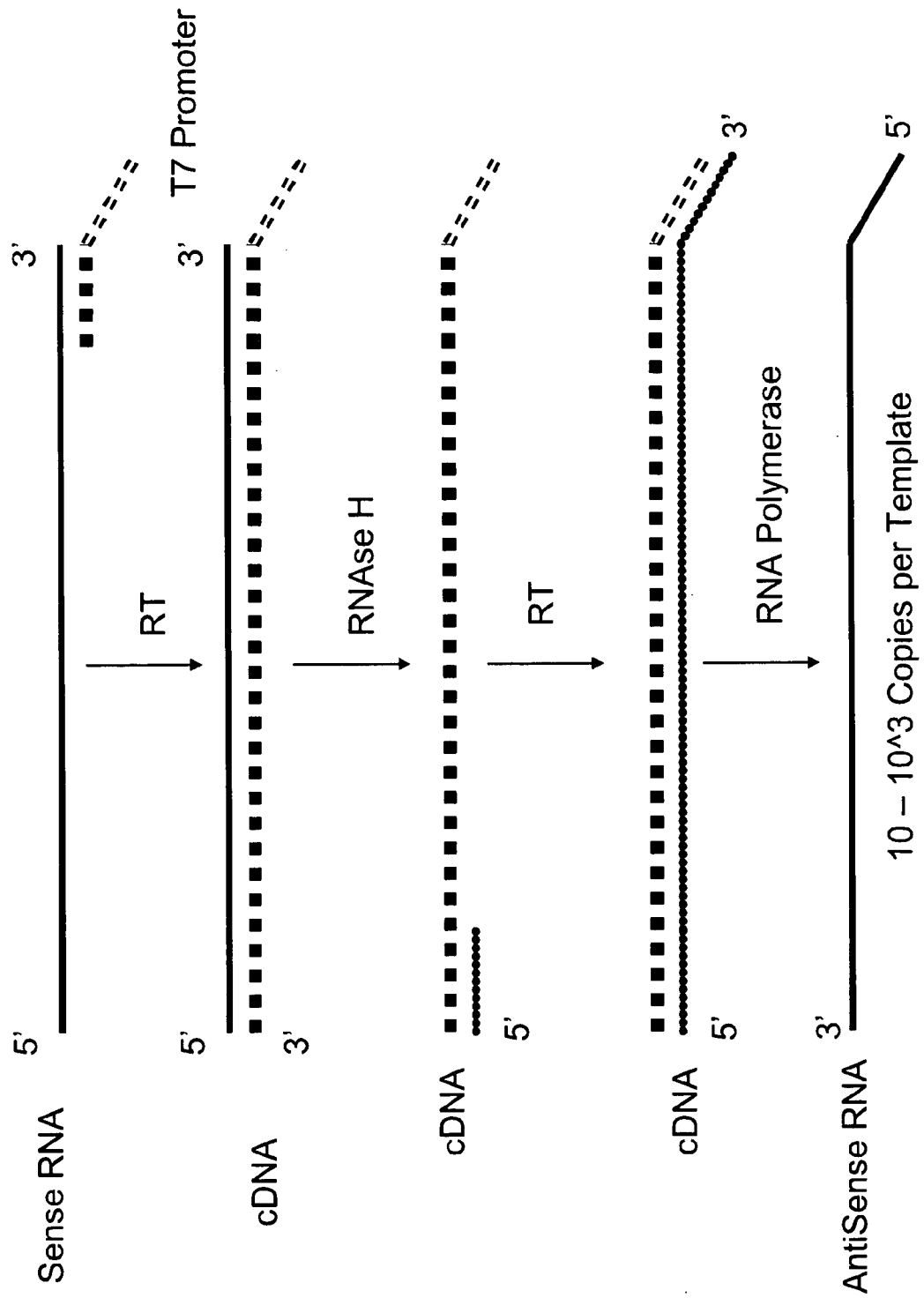
FIG. 9—Depicts amplification of mRNA according to known transcription amplification methods.
Figure 10:
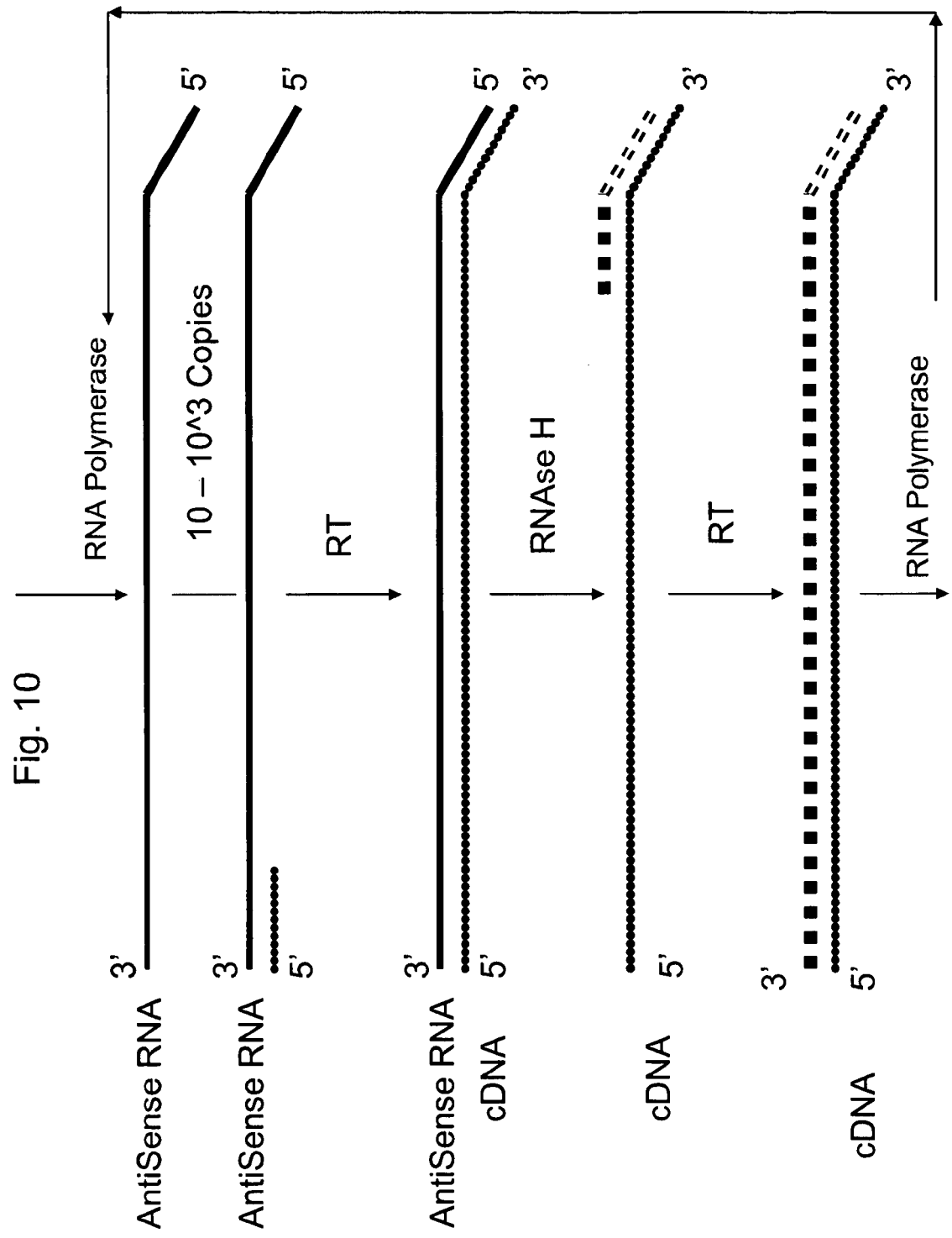
FIG. 10—Depicts further amplification of mRNA according to known transcription amplification methods.
Figure 11:
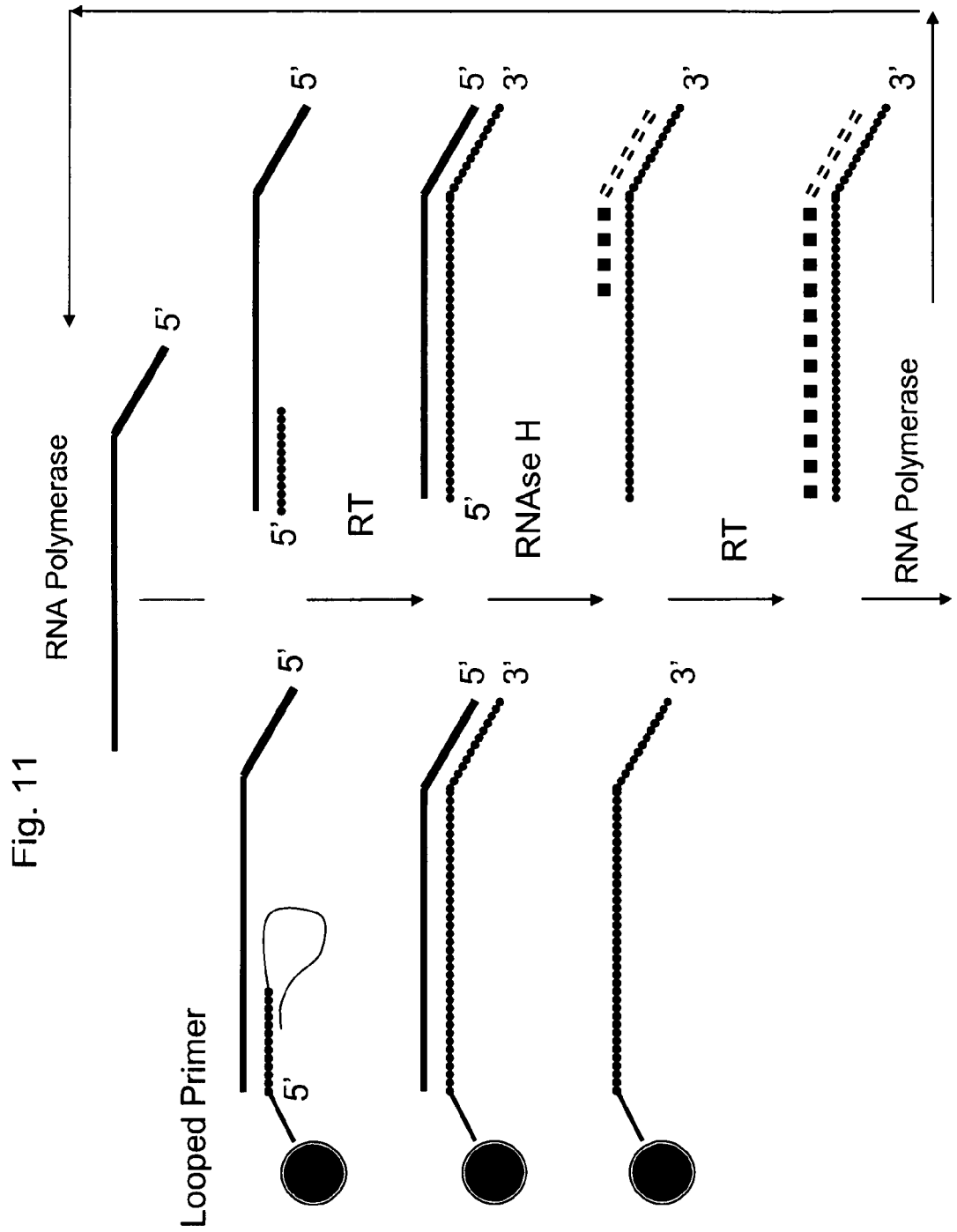
FIG. 11—Depicts, on the left side of the figure, detection of the amplified mRNA using a looped probe attached to a microparticle, which probe is elongated.
Figure 12:
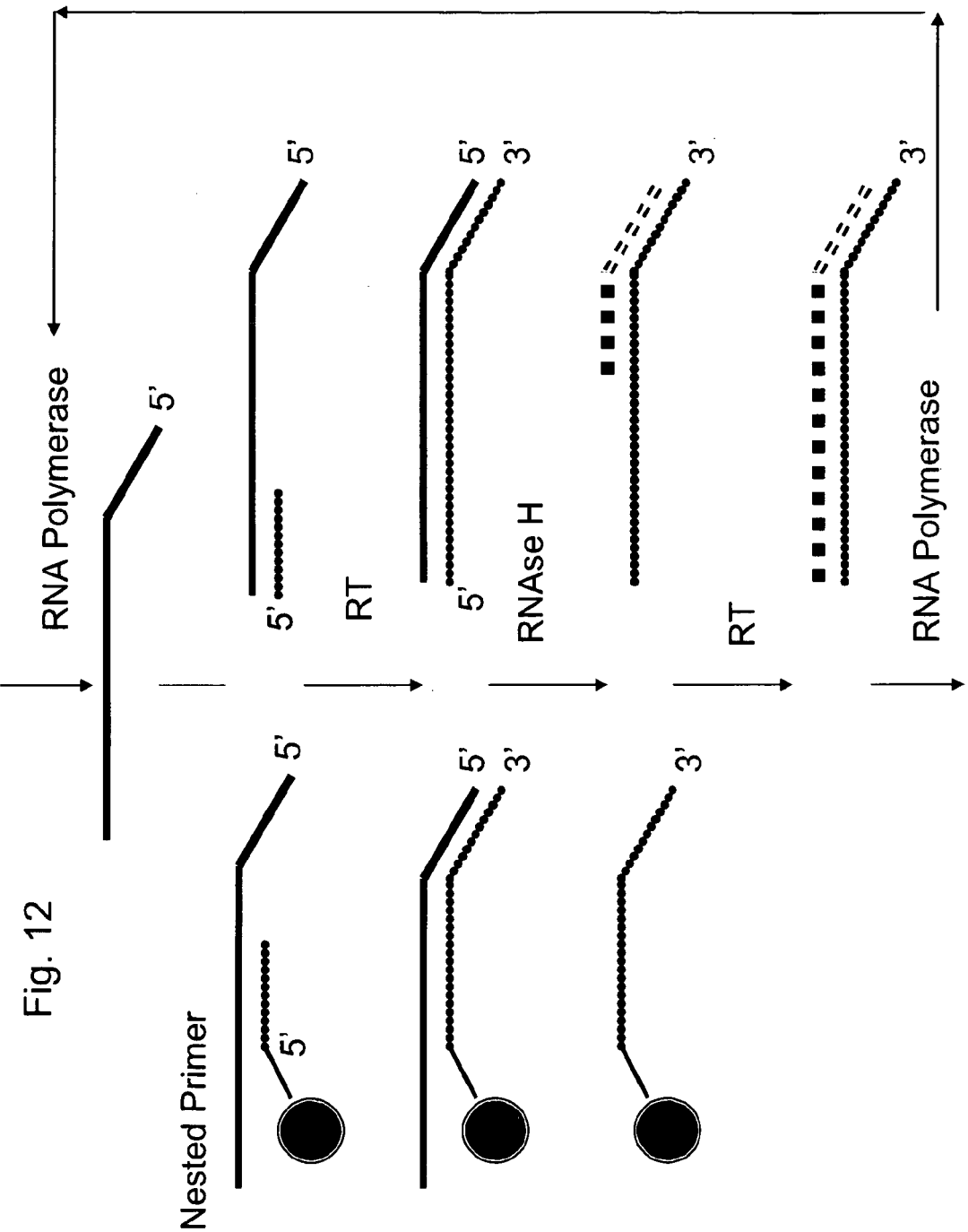
FIG. 12—Depicts, on the left side of the figure, detection of the amplified mRNA using a looped probe attached to a microparticle, which probe is elongated, and where the probe is captured by an mRNA sequence other than the sequence which is complementary to the primer.

Referring to FIGS. 11 and 12, the right-hand side of the figures depicts the process of self-sustained sequence replication. Starting with a RNA sequence and reverse transcriptase (RT), along with a primer sequence complementary to a region at or near the 3' end of the mRNA and also containing an RNA polymerase promoter sequence, is used to synthesize a first cDNA strand. Thereafter, RNAase H is used to digest the RNA in the RNA-cDNA hybrid. Along with reverse transcriptase (RT), a second primer, complementary to a region at or near the 3' end of the cDNA, is used to synthesize a second cDNA strand, complementary to the first cDNA strand. Then, RNA polymerase catalyzes the synthesis of multiple copies of RNA, of which a certain fraction is recycled as a template for additional cDNA synthesis in a self-sustaining "coupled" reaction. This transcription amplification system is described in U.S. Pat. No. 5,399,491; and in Guatelli et al., Proc. Nat'l Acad. Sci. USA, 87: 1874-78 (1990) (both being incorporated by reference) and also shown in FIGS. 9 and 10. The left-hand side of FIGS. 11 and 12 depict detection of a particular subsequence in the sample. FIG. 11 depicts detection using a looped probe which anneals to a subsequence at the 3' end of the nucleic acid sequence (RNA in the figure) and is then elongated, wherein the elongation product can be detected, in accordance with the methods described in International Application No. WO/03034029. FIG. 12 depicts detection using a nested probe, which anneals to a subsequence internal to the nucleic acid sequence (RNA in the figure), and is then elongated. The looped probe on the left-hand side of FIG. 11 can be detected by determining when the probe is in the "closed loop" configuration (before capture and elongation) and when the probe is in the "open loop" configuration. The closed loop configuration of the probe is stabilized by formation of a duplex structure between two complementary subsequences, one located near the 3' end of the probe and a second one near the 5' end of the probe. The subsequence near the 3' end of the probe is also complementary to a subsequence in the nucleic acid being detected. Thus, the probe will open and anneal to the subsequence in the nucleic acid being detected, and can then be elongated. Standard methods invoking fluorescence energy transfer between a donor-acceptor pair of dyes, or related constructs, are available to detect differences in signals from open loop and closed loop configurations of probes in the analyte solution.

Another method of detecting elongation products comprises tagged probes directed to subsequences within the newly formed elongation product. The nested probe on the left-hand side of FIG. 12 is useful to detect unique subsequences, specifically, subsequences comprising polymorphic sites in an amplified nucleic acid sequence. The nested probe would target such a unique subsequence specifically, and elongation would only occur in the event such unique subsequence was present in the sample. As noted above, another use for the assay system of FIGS. 11 and 12 is in a homogeneous assay for detection of reverse transcriptase enzyme in a sample, for example, a sample derived from a cell lysate. Such an assay system is the same as that set forth on the left-hand side of FIGS. 11 and 12, except that no reverse transcriptase is added to the reaction. Unless reverse transcriptase is present in the sample, the amplification reaction will not proceed. FIG. 13 depicts capture of a nucleic acid (including mRNA) to color-encoded magnetic beads (P1 . . . Pn, by means of sequence-specific capture probes, with different probes displayed on different bead types P1 . . . Pn. Following capture, the probes are elongated to form, for example, cDNA strands, and a magnetic field is applied to form a planar array. This allows detection of nucleic acid sequences of interest in a real-time assay, as the array can be read, elongation can be detected, and elongation products can be identified by decoding of the color-code of specific beads, in real-time.

It should be understood that the terms, expressions and example herein are exemplary only, and not limited, and that the invention is defined only in the claims which follow, and includes all equivalents of the subject matter of the claims. The method steps in the claims are not necessarily set forth in order and, unless specified in the claim, the methods in the claims cover steps carried out in any order, including that set forth in the claims.

What is claimed is:

1. A method of selecting probes for analysis of a set of designated nucleic acid sequences by means of a sequence of a first step of selective conversion of cognate nucleic acid subsequences in the designated set of sequences into a related second set of converted sequences using a set of conversion probes, wherein members of the set of conversion probes include a subsequence which is complementary to the cognate nucleic acid subsequences and a second step of capturing said converted sequences to a set of detection probes, wherein members of the set of detection probes include a subsequence which is complementary to cognate target subsequences in the converted sequences, the method comprising:

providing said set of nucleic acid sequences;

performing an iterative optimization of selected probes as follows:

providing an initial set of conversion probes with members which include a subsequence which is complementary to said cognate nucleic acid subsequences;

establishing a first interaction matrix designed such that the cognate nucleic acid subsequences and their respective complementary conversion probes form a diagonal in the matrix, representing the sequence homologies of said subsequences to other subsequences in said set of nucleic acid sequences, wherein said other cognate nucleic acid subsequences represent non-cognate alignments of the conversion probes with the nucleic acid sequences;

reducing the respective sequence homologies of the complementary subsequences to said other cognate nucleic acid subsequences, by removing at least one of the conversion probes from the set and substituting a different conversion probe in the set;

providing an initial set of detection probes with members which include a subsequence which is complementary to cognate target subsequences;

establishing a second interaction matrix, designed such that the cognate target subsequences and their respective complementary detection probes form a diagonal in the matrix, representing the sequence homologies of said cognate target subsequences to other converted subsequences in said set of converted sequences, wherein said other converted subsequences represent non-cognate alignments of the detection probes with the converted sequences;

reducing the respective sequence homologies of the complementary cognate target subsequences to said other converted subsequences by removing at least one of the detection probes from the set and substituting a different detection probe in the set;

evaluating convergence criteria for values of off-diagonal elements in the first and second interaction matrices in relation to preset convergence criteria; and for conversion probes and detection probes in the matrices not satisfying the convergence criterion, iterating the sequence of steps, removing and substituting until convergence is attained;

outputting the set of conversion probes and the set of detection probes satisfying the convergence criteria to a display; and using the set of detection probes satisfying the convergence criteria to perform analysis of the set of nucleic acid sequences in an assay wherein members of the set of detection probes hybridize with members of the set of nucleic acid sequences, which is detected.

2. The method of claim 1 wherein the convergence criterion is a threshold sequence similarity score for said cognate nucleic acid subsequences to said other cognate nucleic acid subsequences and a threshold similarity score for said complementary cognate target subsequences to said other converted subsequences.

3. The method of claim 1 wherein the converted sequences include sense and anti-sense converted sequences and at least one antisense detection probe is selected which include a subsequence which is complementary to a cognate target subsequence in a sense converted sequence, and at least one antisense detection probe is selected which includes a subsequence which is complementary to a cognate target subsequence in an antisense converted sequence.

4. The method of claim 3 further including the step of selecting, for detecting the presence of at least one converted subsequence, either a sense detection probe or an anti-sense detection probe, based on which probe selection results in a similarity score below threshold of said complementary cognate target subsequences to said other converted subsequences.

5. The method of claim 1 wherein said other subsequences in the first interaction matrix are subsequences which are cognate to other conversion probes in the first interaction matrix.

6. The method of claim 1 wherein said other subsequences in the second interaction matrix are subsequences which are cognate to other detection probes in the second interaction matrix.

7. The method of claim 1 wherein the nucleic acid sequences are mRNA and the converted sequences are cDNA.

8. The method of claim 1 wherein the nucleic acid sequences are DNA and the converted sequences are DNA.

9. The method of claim 1 wherein nucleic acid sequences are RNA and DNA transcripts are generated and then used to produce RNA.

10. The method of claim 1 further including the step of selecting either a sense conversion probe, which hybridizes to the cognate antisense subsequence in the nucleic acid sequence, or the anti-sense conversion probe, which hybridizes to the cognate sense subsequence in the nucleic acid sequence, based on an end-weighted Hamming distance function similarity score, wherein mismatches in the subsequences, which are aligned with the region at or near the 3' end of the conversion probe have a further reduced sequence homology score.

* * * * *

SEQUENCE LISTING

<160> NUMBER OF SEQ ID NOS: 117

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
attgggcgtc agaattgtcg                                                  20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
atgttgaagc catcattacc attc                                             24

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggacgaggac gaggaggt                                                    18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tgtcctgctg tcaccaagag                                                  20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctaatggga accgggc                                                     17

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cagtgtgtgt agagagccgg                                         20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctttagcac tccttggcaa a                                       21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gtgtaggcac tgaggacgg                                          19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgagcgtct gagccaaga                                          19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
atgctgccgt gcctcgtag                                          19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcatagtatt ctctgagccg g                                       21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
caggtggcat ttacacccta cg                                      22

```
<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcttgccgg taagggtt                                                   18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gcaggatcct ggtatccgct a                                               21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acggtgccat ggaatttgc                                                  19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
ggagtcaacg gatttggtcg t                                               21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtgtaggcac tgaggacgg                                                  19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gcatggctct cctctttctc c                                               21

<210> SEQ ID NO 19
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tacaagcttg ggcgtgtctc                                            20

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccgcgctgtc ctgctgtcac caagagctgg agacaccatc tcccaccgag agtcat    56

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cggcgcgggg ccgagggact cgcagtgtgt gtagagagcc gggctcctgc ggatgggggc 60

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggccccattg gccctgcacc tcctcgtcct cgtccccatc ctcctcag              48

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgccccgggg gcctgagccc gcctgcccgc ccaccgcccc gccc                  44

<210> SEQ ID NO 24
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggcgcgggg ccgagggact cgcagtgtgt gtagagagcc gggctcctgc ggatgggg   58

<210> SEQ ID NO 25
<211> LENGTH: 54
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25
cgcgcaggcc ggctccgctc cggccccgga cgatgcggcg cgcccaggat gctg          54

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gctgcccccg gggcctgagc ccgcctgccc gcccaccgcc ccgccc                   46

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccgtgcctcg tagtgctgct ggcggcgctc ctcagcctcc gtcttggctc               50

<210> SEQ ID NO 28
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(52)
<223> OTHER INFORMATION: a, c, g, t, unknown or other

<400> SEQUENCE: 28
ttcgacagtc agccgcatct tcttttgcgt cgccagccga gccacatcgc tnag          54

<210> SEQ ID NO 29
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccagcgaccg tcggtagcag catggctctc ctctttctcc taccccttgt catgcag       57

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
acaccatggg gaaggtgaag gtcggagtca acggatttgg tcgtattggg cg            52

<210> SEQ ID NO 31
```

```
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggtgtgagca gggctgagat gggcaccgcg gatctggggc cgtcctcag                49

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tggacgtggt tggtgattgg caggatcctg gtatccgcta acaggtcaaa atgcag        56

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(52)
<223> OTHER INFORMATION: a, c, g, t, unknown or other

<400> SEQUENCE: 33
ttcgacagtc agccgcatct tcttttgcgt cgccagccga gccacatcgc tn            52

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atcttcgtga aaacccttac cggcaagacc atcacccttg aggtggagc                49

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agacaccatg gggaaggtga aggtcggagt caacggattt ggtcgtattg ggcg          54

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccgcgctgtc ctgctgtcac caagagctgg agacaccatc tcccaccgag agtc          54
```

<210> SEQ ID NO 37
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cggcgcgggg ccgagggact cgcagtgtgt gtagagagcc gggctcctgc ggatgggg        58

<210> SEQ ID NO 38
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgcgcaggcc ggctccgctc cggccccgga cgatgcggcg cgcccaggat gctg            54

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tggacgtggt tggtgattgg caggatcctg gtatccgcta acaggtcaaa                 50

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccagcgaccg tcggtagcag catggctctc ctctttctcc taccccttgt c               51

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (52)..(52)
<223> OTHER INFORMATION: a, c, g, t, unknown or other

<400> SEQUENCE: 41
ttcgacagtc agccgcatct tcttttgcgt cgccagccga gccacatcgc tnag            54

<210> SEQ ID NO 42
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
atggccccat tggccctgca cctcctcgtc ctcgtcccca tcctcctca                49
```

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
gctgcccccg gggcctgagc ccgcctgccc gcccaccgcc ccgccc                  46
```

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
ccgtgcctcg tagtgctgct ggcggcgctc ctcagcctcc gtcttggctc               50
```

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
atgcagatct tcgtgaaaac ccttaccggc aagaccatca cccttga                 47
```

<210> SEQ ID NO 46
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
atgcagggtg tgagcagggc tgagatgggc accgcggatc tggggccgtc ctca         54
```

<210> SEQ ID NO 47
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
acaccatggg gaaggtgaag gtcggagtca acggatttgg tcgtattgg                49
```

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
attgggcgtc agaattgtcg                                                20
```

-continued

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
atgttgaagc catcattacc attc                                          24

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggacgaggac gaggaggt                                                 18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
tgtcctgctg tcaccaagag                                               20

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctaatggga accgggc                                                  17

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
cagtgtgtgt agagagccgg                                               20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tctttagcac tccttggcaa a                                             21

<210> SEQ ID NO 55

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
gtgtaggcac tgaggacgg                                              19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atgagcgtct gagccaaga                                              19

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
atgctgccgt gcctcgtag                                              19

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcatagtatt ctctgagccg g                                           21

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
caggtggcat ttacaccctc cg                                          22

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtcttgccgg taagggtt                                               18

<210> SEQ ID NO 61
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 61
gcaggatcct ggtatccgct a                                              21

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acggtgccat ggaatttgc                                                 19

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
ggagtcaacg gatttggtcg t                                              21

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtgtaggcac tgaggacgg                                                 19

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
gcatggctct cctctttctc c                                              21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
tacaagcttg ggcgtgtctc                                                20

<210> SEQ ID NO 67
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 67
ccctgcacct cctcgtcc                                                    18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acctcctcgt cctcgtcc                                                    18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acctcctcgt cctcgtcc                                                    18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acctcctcgt cctcgtcc                                                    18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tcgtcctcgt ccccatcc                                                    18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acctcctcgt cctcgtcc                                                    18

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 73
gcccggttcc cattagc                                               17

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcccggttcc cattagc                                               17

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcccggaggc catgggc                                               17

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcccggttcc cattagc                                               17

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tcttggctca gacgctcat                                             19

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tcttggctca gacgctcat                                             19

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
```
aacccttacc ggcaagac         18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aacccttacc ggcaagac         18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gaccctgacc ggcaagac         18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
aacccttacc ggcaagac         18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gaccctgacc ggcaagac         18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
aacccttacc ggcaagac         18

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gcaaattcca tggcaccgtc a         21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
gcaaattcca tggcaccgtc a                           21

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
ccgtcctcag tgcctacac                              19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
ccgtcctcag tgcctacac                              19

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
cgacaattct gacgcccaat g                           21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
cgacaattct gacgcccaat g                           21

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
gtctgcacgt ccacgtcc                               18

```
<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
acctcctcgt cctcgtcc                                                   18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acgtccacgt cccccacc                                                   18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
acctcctcgt cctcgtcc                                                   18

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccggctcaga gaatactatg a                                               21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ccggctcaga gaatactatg a                                               21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tttgccaagg agtgctaaag a                                               21

<210> SEQ ID NO 98
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tttgccaagg agtgctaaag a                                                   21

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
tgtcctgctg tcaccaagag                                                     20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
tgtcctgctg tcaccaagag                                                     20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
cagtgtgtgt agagagccgg                                                     20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
cagtgtgtgt agagagccgg                                                     20

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
atgctgccgt gcctcgtag                                                      19

<210> SEQ ID NO 104
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 104
atgctgccgt gcctcgtag                                                  19

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
gcaggatcct ggtatccgct a                                               21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
gcaggatcct ggtatccgct a                                               21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
ggagtcaacg gatttggtcg t                                               21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
ggagtcaacg gatttggtcg t                                               21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
tctcctaccc cttgtcatgc                                                 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued probe

<400> SEQUENCE: 110
tctcctaccc cttgtcatgc                                        20

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
gttgaagcca tcattaccat tcaca                                  25

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
gttgaagcca tcattaccat tcaca                                  25

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
caggtggcat ttacacccta cg                                     22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
caggtggcat ttacacccta cg                                     22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
gcagagcaca caagcttcta gg                                     22

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 116
gcagagcaca caagcttcta gg                                              22

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cccccccccc cccccccc                                                   18
```